US009045440B2

(12) United States Patent
Malecha

(10) Patent No.: US 9,045,440 B2
(45) Date of Patent: Jun. 2, 2015

(54) DESAZADESFERROTHIOCIN AND DESAZADESFERROTHIOCIN POLYETHER ANALOGUES AS METAL CHELATION AGENTS

(75) Inventor: James Malecha, San Diego, CA (US)

(73) Assignee: FerroKin Biosciences, Inc., Wayne, PA (US)

(*) Notice: Subject to any disclaimer, the term of this patent is extended or adjusted under 35 U.S.C. 154(b) by 764 days.

(21) Appl. No.: 13/100,705

(22) Filed: May 4, 2011

(65) Prior Publication Data

US 2011/0275636 A1 Nov. 10, 2011

Related U.S. Application Data

(60) Provisional application No. 61/331,138, filed on May 4, 2010.

(51) Int. Cl.

| C07D 231/14 | (2006.01) |
| C07D 233/28 | (2006.01) |
| C07D 263/16 | (2006.01) |
| C07D 277/12 | (2006.01) |
| C07D 277/56 | (2006.01) |
| A61K 31/5377 | (2006.01) |
| A61K 31/421 | (2006.01) |
| A61K 31/4172 | (2006.01) |
| A61K 31/426 | (2006.01) |
| A61K 31/496 | (2006.01) |

(52) U.S. Cl.
CPC ............ *C07D 263/16* (2013.01); *C07D 231/14* (2013.01); *C07D 233/28* (2013.01); *C07D 277/12* (2013.01); *C07D 277/56* (2013.01)

(58) Field of Classification Search
None
See application file for complete search history.

(56) References Cited

U.S. PATENT DOCUMENTS

| 4,457,936 | A | 7/1984 | Draeger et al. |
| 6,083,966 | A | 7/2000 | Bergeron, Jr. |
| 8,063,227 | B2 | 11/2011 | Tapper |
| 2004/0132789 | A1 | 7/2004 | Bergeron, Jr. |
| 2005/0101782 | A1 | 5/2005 | Krich et al. |
| 2006/0069134 | A1 | 3/2006 | Maruoka et al. |
| 2006/0211746 | A1 | 9/2006 | Bergeron |
| 2008/0093812 | A1 | 4/2008 | Reed et al. |
| 2008/0096974 | A2 | 4/2008 | Bergeron |
| 2008/0138440 | A1 | 6/2008 | Swaminathan et al. |
| 2008/0214630 | A1 | 9/2008 | Bergeron |
| 2010/0093812 | A1 | 4/2010 | Bergeron, Jr. |
| 2010/0137346 | A1 | 6/2010 | Bergeron |
| 2010/0137383 | A1 | 6/2010 | Tapper et al. |
| 2011/0053993 | A1 | 3/2011 | McCall, Jr. |
| 2011/0160257 | A1 | 6/2011 | Tapper |
| 2012/0202857 | A1 | 8/2012 | Tapper |
| 2012/0270911 | A1 | 10/2012 | Tapper |
| 2013/0005781 | A1 | 1/2013 | McCall, Jr. |

FOREIGN PATENT DOCUMENTS

| CN | 101687825 A | 3/2010 |
| CN | 101928281 A | 12/2010 |
| EP | 0033151 A1 | 8/1981 |
| JP | 2005-289890 A | 10/2005 |
| WO | 0012493 A1 | 3/2000 |
| WO | WO-00/62777 A1 | 10/2000 |
| WO | 2005023310 | 3/2005 |
| WO | 2005034949 A1 | 4/2005 |
| WO | 2006107626 | 10/2006 |
| WO | 2008115433 | 9/2008 |
| WO | 2008130395 | 10/2008 |
| WO | 2010009120 | 1/2010 |
| WO | 2010009120 A3 | 1/2010 |
| WO | 2011017054 A2 | 2/2011 |
| WO | 2011028255 A2 | 3/2011 |

OTHER PUBLICATIONS

Bergeron RJ, Wiegand J, McManis JS, Bharti N and Singh, S: Desferrithiocin analogue iron chelators: iron clearing efficiency, tissue distribution, and renal toxicity, Biometals, Nov. 2010 epub only: http://www.springerlink.com/content/p5254pq117818l12/.
Caira MR, Crystalline Polymorphism of Organic Compounds, Topics in Current Chemistry, vol. 198, Jan. 1, 1998, pp. 163-208.
Bergeron, R.J. et al., Design, Synthesis, and Testing of Non-Nephrotoxic Desazadesferrithiocin Polyether Analogues, J. Med. Chem., (2008), pp. 3913-3923, 51.
Bergeron, R.J. et al., Polyamine-Vectored Iron Chelators: The Role of Charge, J. Med. Chem., (2005), pp. 4120-4137, 48.
Bergeron, R.J. et al., (S)-4,5-Dihydro-2-(2-hydroxy-4-hydroxyphenyl)-4-methyl-4-thiazolecarboxylic Acid Polyethers: A Solution to Nephrotoxicity, J. Med. Chem., (2006), pp. 2772-2783, 49.
Bergeron, R.J. et al., Impact of the 3,6,9-Trioxadecyloxy Group on Desazadesferrithiocin Analogue Iron Clearance and Organ Distribution, J. Med. Chem., (2007), pp. 3302-3313, 50.
Bergeron, R.J. et al., Iron Chelation Promoted by Desazadesferrithiocin Analogs: An Enantioselective Barrier, Chirality, (2003), pp. 593-599, 15 (7).
Bergeron, R.J. et al., The Impact of Polyether Chain Length on the Iron Clearing Efficiency and Physiochemical Properties of Desferrithiocin Analogues, J. Med. Chem., (2010), pp. 2843-2853, 53.
Bergeron, R.J. et al., Desferrithiocin Analogue Iron Chelators: Iron Clearing Efficiency, Tissue Distribution, and Renal Toxicity, Biometals, (e-publication only), http://www.springerlink.com/content/p5254pq117818l12/, Nov. 2010.
Bergeron, R.J. et al., The Design, Synthesis, and Evaluation of Organ-Specific Iron Chelators, (2006), pp. 7032-7043, 49.

(Continued)

*Primary Examiner* — Alicia L Otton
(74) *Attorney, Agent, or Firm* — Choate, Hall & Stewart, LLP; Fangli Chen; John P. Rearick

(57) ABSTRACT

Disclosed herein are new compounds of desazadesferrothiocin polyether (DADFT-PE) analogs, as well as pharmaceutical compositions comprising them and their application as metal chelation agents for the treatment of disease. Methods of chelation of iron and other metals in a human or animal subject are also provided for the treatment of metal overload and toxicity.

14 Claims, No Drawings

(56) References Cited

OTHER PUBLICATIONS

Bergeron, R.J. et al., A comparative study of the iron-clearing properties of desferrithiocin analogues with desferrioxamine B in a *Cebus* monkey model, Blood, 81(8): 2166-2173 (1993).

Bergeron, R.J. et al., A comparative evaluation of iron clearance models, Ann. N.Y Acad.Sci., 612: 378-393 (1990).

Bergeron, R.J. et al., Comparison of iron chelator efficacy in iron-overloaded beagle dogs and monkeys (*Cebus apella*), Comp. Med., 54(6): 664-672 (2004).

Bergeron, R.J. et al., Effects of C-4 stereochemistry and C-4' hydroxylation on the iron clearing efficiency and toxicity of desferrithiocin analogues, J. Med. Chem., 42(13): 2432-2440 (1999).

Bergeron, R.J. et al., Impact of the Lipophilicity of Desferrithiocin Analogues on Iron Clearance, Medicinal Inorganic Chemistry, 366-383 (2005).

European Search Report for 11778269, 2 pages (Sep. 24, 2013).

Hanson, L.R. and Frey, W.H. 2nd, Strategies for intranasal delivery of therapeutics for the prevention and treatment of neuroAIDS, J. Neuroimmune Pharmacol., 2(1): 81-6 (2007).

International Search Report for PCT/US11/35211, 5 pages (Jan. 6, 2012).

Rao, L. et al., Complexation of thorium(IV) with desmethyldesferrithiocin, Radiochim. Acta., 88: 851-856 (2000).

Weininger, D., Smiles, a chemical language and information system. 1. Introduction to methodology and encoding rules, J. Chem. Inf. Comput. Sci., 28(1): 31-36 (1988).

Written Opinion for PCT/US11/35211, 7 pages (Jan. 6, 2012).

DESAZADESFERROTHIOCIN AND DESAZADESFERROTHIOCIN POLYETHER ANALOGUES AS METAL CHELATION AGENTS

This application claims the benefit of priority of U.S. provisional application No. 61/331,138, filed May 4, 2010, the disclosure of which is incorporated by reference as if written herein in its entirety.

Disclosed herein are desazadesferrothiocin (DADFT) and desazadesferrothiocin polyether (DADFT-PE) analogues, as well as pharmaceutical compositions comprising them and their application as metal chelation agents for the treatment of disease. Methods of chelation of iron and other metals in a human or animal subject are also provided for the treatment of metal overload and toxicity.

Metal ions are critical to the proper functioning of living systems. Ions such as $Fe^{3+}$, $Zn^{2+}$, $Cu^{2+}$, $Ca^{2+}$, and $Co^{3+}$, to name but a few, can be found in the active sites of over a third of known enzymes and other functional proteins such as RNA polymerase, DNA transcription factors, cytochromes $P_{450}s$, hemoglobin, myoglobin, and coenzymes such as vitamin $B_{12}$. There, these metals serve to facilitate oxidation and reduction reactions, stabilize or shield charge distributions, and orient substrates for reactions.

However, the body has a limited ability to absorb and excrete metals, and an excess can lead to toxicity. As one example, an excess of iron, whether derived from red blood cells chronically transfused, necessary in such conditions such as β-thalassemia major, or from increased absorption of dietary iron such as hereditary hemochromatosis caused by mutation in genes such as HFE can be toxic through the generation by iron of reactive oxygen species such as $H_2O_2$. In the presence of $Fe^{2+}$, $H_2O_2$ is reduced to the hydroxyl radical (HO), a very reactive species, a process known as the Fenton reaction. The hydroxyl radical reacts very quickly with a variety of cellular constituents and can initiate free radicals and radical-mediated chain processes that damage DNA and membranes, as well as produce carcinogens. The clinical result is that without effective treatment, total body iron progressively increases with deposition in the liver, heart, pancreas, and elsewhere. Iron accumulation may also produce (i) liver disease that may progress to cirrhosis, (ii) diabetes related both to iron-induced decreases in pancreatic β-cell secretion and increases in hepatic insulin resistance and (iii) heart disease, still the leading cause of death in β-thalassemia major and other anemias associated with transfusional iron overload.

As another example, relative excess iron has been associated with increased risk of heart disease. There is a strong correlation between serum ferritin levels, inflammatory biomarkers such as C-reactive protein and interleukin-1, and mortality is a subset of patients with peripheral arterial disease; phlebotomy and iron chelation has been used to mitigate that risk. Treatment with an iron chelator would reduce iron stores, reduce serum ferritin and potentially reduce the incidence of heart disease and stroke.

As another example, ions with little or no endogenous function may find their way into the body and effect damage. Heavy metal ions such as $Hg^{2+}$ can replace ions such as $Zn^{2+}$ in metalloproteins and render them inactive, resulting in serious acute or chronic toxicity that can end in a patient's death or in birth defects in that patient's children. Even more significantly, radioactive isotopes of the lanthanide and actinide series can visit grave illness on an individual exposed to them by mouth, air, or skin contact. Such exposure could result not only from the detonation of a nuclear bomb or a "dirty bomb" composed of nuclear waste, but also from the destruction of a nuclear power facility.

Agents for the chelation and decorporation of metal ions in living organisms have been previously disclosed and are in clinical use. A variety of ligands have been shown to bind $Fe^{3+}$, $Pu^{4+}$, $Th^{4+}$, $Am^{4+}$, $Eu^{3+}$ and $U^{4+}$, for example. Traditional standard therapies include the use of agents such as deferoxamine (DFO, N'-[5-(acetyl-hydroxy-amino)pentyl]-N-[5-[3-(5-aminopentyl-hydroxy-carbamoyl)propanoylamino]pentyl]-N-hydroxy-butane diamide), a very effective metal chelator. DFO is, unfortunately, not orally bioavailable and must therefore be parenterally dosed IV, IP, or SC, and once in the bloodstream has a very short half life. Diethylene triamine pentaacetic acid (DTPA) is approved for use in the treatment of lanthanide and actinide poisoning, but also cannot be dosed orally, ideally should be given very quickly following contamination, and presents with a number of side effects. For these reasons, continuous infusion of these agents is often required, and particularly in the case of chronic disorders, patient compliance can be a problem. A thorough review of publicly available art will show that although effective chelation agents have been available for decades, oral bioavailability has historically been a desirable trait in successive next-generation agents.

More recently, orally active agents have become available for use in the treatment of metal overload. Deferiprone (3-hydroxy-1,2-dimethylpyridin-4(1H)-one) has been used in Europe and some other countries as an oral agent for the treatment of transfusional iron overload in the setting of beta thalassemia and other disorders, but the drug is not approved for use in the United States and Canada, and reported side effects including agranulocytosis have in many cases relegated it to second-line therapy. Deferasirox (Exjade, [4-[(3Z,5E)-3,5-bis(6-oxo-1-cyclohexa-2,4-dienylidene)-1,2,4-triazolidin-1-yl]benzoic acid, Novartis) is currently the only oral agent approved in the United States for chelation therapy. Even still, nephrotoxicity leading to renal failure and cytopenia have been reported by the Food and Drug Administration as side effects to Deferasirox oral suspension tablets. Moreover, neither of these agents is as efficacious a chelator as DFO. Clearly, a need still exists in the art for long-lasting, orally active metal chelators with reduced toxicity for the treatment of iron overload secondary to transfusion or excessive intestinal absorption and other metal overload disorders.

Analogues of desferrithiocin, or [(S)-4,5-dihydro-2-(3-hydroxy-2-pyridinyl)4methyl-4thiazo]carboxylic acid (DFT) have been shown to form 2:1 hexacoordinate complexes with $Fe^{3+}$ and $Th^{4+}$. These ligands, when administered either subcutaneously (SC) or orally (PO) to rodents, dogs, and primates, have been shown to clear iron very efficiently, and to decorporate uranium from rodents when given SC, PO, or intraperitoneally, with particularly profound effects in the kidney. Although development of DFT itself had been discontinued due to nephrotoxicity, one of these ligands (S)-2-(2,4-dihydroxyphenyl)4,5dihydro-4-methyl-4-thiazolecarboxylic acid, or (S)-4'-(HO)-DADFT, has proven to be an effective chelation agent with the additional benefit of being orally available, and as of the present is believed to be in clinical trials. A recent paper discloses the design and testing of DADFT analogues substituted by a polyether group at the 3', 4', and 5' positions (Bergeron R J et al., *J Med Chem.* 2007 Jul. 12; 50(14):3302-13). Polyether analogues had uniformly higher iron-clearing efficiencies (ICEs) than their corresponding parent ligands in rodents and in serum albumin binding studies, with the 3'-DADFT-PE analogue (S)-4,5-dihydro-2-[2-hydroxy-3-(3,6,9-trioxadecyloxy)phenyl]-4- methyl-4-thiazolecarboxylic acid showing the most promising ICE in rodents and non-human primates.

Though DADFT polyethers as a class of compounds appear promising in the search for improved metal chelation agents, much work remains to be done in the characterization, development, and selection of a compound suitable for use in humans. Room for improvement is still apparent in the design of analogues which have the optimal balance of bioavailability and other pharmacokinetic parameters, solubility, ICE or other metal-clearing efficacy, favorable metabolism and toxicology, and other attributes for the purpose of providing safe and effective compounds which will be easy to use by patients and clinicians alike. Additionally, many factors still influence the suitability of a compound as a pharmaceutical agent in general. For example, to be ideally suited for delivery to patients, compounds should be readily uptaken by the patient's body via the chosen route of administration, should be soluble and bioavailable to the target compartment or organ, and should be cleared from the body in an appropriate period of time.

Disclosed herein are novel DADFT and DADFT-PE analogues and derivatives thereof. Pharmaceutical formulations comprising these compounds are also disclosed, as well as methods for the treatment of diseases and conditions related to toxicity which is a result of an acute or chronic excess of metal in a human or animal body.

In certain embodiments, compounds have the structural formula I:

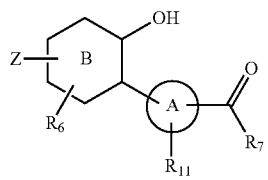

I wherein:
A is a five or six membered heterocycle;
B is chosen from phenyl, naphthyl and quinolinyl;
Z is chosen from $OR_1$, $NR_2R_3$, morpholine and optionally substituted piperazine;
$R_1$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_n-O]_x-[(CH_2)_n-NR_4]_y-R_5$;
$R_2$ is chosen from hydrogen, alkyl, $[(CH_2)_m-O]_x-[(CH_2)_n-O]_y-R_4$, and $[(CH_2)_m-O]_x-[(CH_2)_n-NR_4]_y-R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $-(CH_2)_p-N(OH)C(O)R_{10}$;
p is an integer from 1 to 8;
$R_{10}$ is an alkyl group;
$R_{11}$ is chosen from hydrogen and alkyl.

Certain compounds and prodrugs disclosed herein may possess useful metal chelating activity, and may be used in the treatment or prophylaxis of a disease or condition in which metal overload or toxicity plays an active role. Thus, in broad aspect, certain embodiments also provide pharmaceutical compositions comprising one or more compound or prodrug disclosed herein together with a pharmaceutically acceptable carrier, as well as methods of making and using the compounds and prodrugs and their compositions. Certain embodiments provide methods for chelating metals in living systems. Other embodiments provide methods for treating disorders and symptoms relating to metal toxicity in a patient in need of such treatment, comprising administering to said patient a therapeutically effective amount of a compound or composition according to the present invention, or a prodrug thereof. Also provided is the use of certain compounds and prodrugs disclosed herein for use in the manufacture of a medicament for the treatment of a disease or condition ameliorated by the chelation or decorporation of metals.

In certain embodiments are provided compounds of Formula I wherein:
$R_1$ is $[(CH_2)_m-O]_x-[(CH_2)_n-O]_y-R_4$; certain
x is 0;
y is an integer from 1 to 8; and
n is 2.
In further embodiments are provided compounds of Formula I wherein y is an integer from 1 to 4.
In other embodiments are provided compounds of Formula I wherein:
$R_1$ is $[(CH_2)_m-NH]_x-[(CH_2)_n-NR_4]_y-R_5$;
x is 0-1;
y is an integer from 1 to 8; and
n is 2 or 3.
In further embodiments are provided compounds of Formula I wherein:
$R_1$ is $[(CH_2)_n-NR_4]_y-R_5$;
y is an integer from 1 to 4; and
n is 3.
In other embodiments are provided compounds of Formula I wherein:
$R_2$ is $[(CH_2)_m-O]_x-[(CH_2)_n-O]_y-R_4$;
X is 0;
y is an integer from 1 to 8; and
n is 2.
In further embodiments are provided compounds of Formula I wherein y is an integer from 1 to 4.
In other embodiments are provided compounds of Formula I wherein:
$R_2$ is $[(CH_2)_m-O]_x-[(CH_2)_n-NR_4]_y-R_5$;
X is 0;
y is an integer from 1 to 8; and
n is 2 or 3.
In further embodiments are provided compounds of Formula I wherein:
$R_2$ is $[(CH_2)_n-NR_4]_y-R_5$;
y is an integer from 1 to 4; and
n is 3.
In other embodiments are provided compounds of Formula I wherein:
$R_2$ is $[(CH_2)_m-NH]_x-[(CH_2)_n-NR_4]_y-R_5$;
x is 0-1;
y is an integer from 1 to 8; and
n is 2 or 3.
In further embodiments are provided compounds of Formula I wherein:
$R_2$ is $[(CH_2)_m-NH]_x-[(CH_2)_n-NR_4]_y-R_5$;
x is 0-1;
y is an integer from 1 to 4; and
n is 2 or 3.

In certain embodiments, compounds have structural formula II:

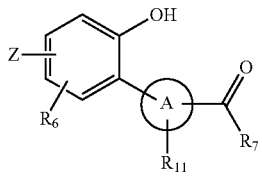

II wherein:
A is a five or six membered heterocycle;
Z is chosen from $OR_1$, $NR_2R_3$, morpholine and optionally substituted piperazine;
$R_1$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_2$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $-(CH_2)_p-N(OH)C(O)R_{10}$;
p is an integer from 1 to 8;
$R_{10}$ is an alkyl group;
$R_{11}$ is chosen from hydrogen and alkyl.

In further embodiments compounds have the structural formula II wherein A is a five membered heterocycle.

In certain embodiments, A has the structural formula

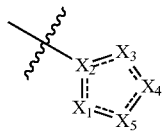

wherein:
each dashed line represents a second bond which may be present or absent;
$X_1$-$X_5$ are each chosen from $CR_{12}$, $NR_{13}$, O, and S, and no more than three of $X_1$-$X_5$ are heteroatoms;
each $R_{12}$ is independently chosen from null, hydrogen, and lower alkyl; and
each $R_{13}$ is independently chosen from null, hydrogen, and lower alkyl.

In further embodiments compounds have the structural formula II wherein A is a five membered heterocycle that does not contain a sulfur atom.

In further embodiments compounds have the structural formula II wherein:
Z is $NR_2R_3$;
$R_2$ is chosen from $[(CH_2)_m-O]_x-[(CH_2)_n-O]_y-R_4$, and $[(CH_2)_m-O]_x-[(CH_2)_n-NR_4]_y-R_5$; and $R_3$ is chosen from hydrogen and alkyl.

In other embodiments compounds have the structural formula II wherein Z is chosen from morpholine and optionally substituted piperazine.

In yet further embodiments compounds have the structural formula II wherein Z is $OR_1$.

In further embodiments compounds have the structural formula II wherein $R_1$ is $[(CH_2)_n-O]_x-[(CH_2)_n-O]_y-R_4$.

In further embodiments compounds have the structural formula II wherein each n is, independently, an integer from 1 to 4; x is an integer from 0 to 4; and y is an integer from 1 to 4.

In further embodiments compounds have the structural formula II wherein $R_4$ is alkyl.

In further embodiments compounds have the structural formula II wherein $R_7$ is $OR_8$.

In yet further embodiments compounds have the structural formula II wherein $R_8$ is hydrogen.

In further embodiments, compounds have structural formula chosen from IIa, IIb, and IIc:

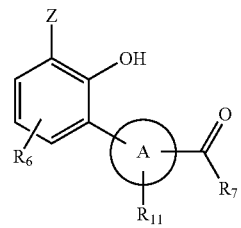

IIa

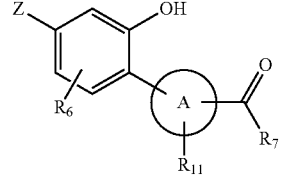

IIb

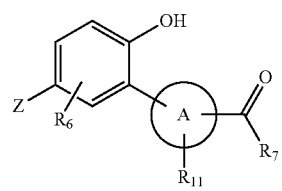

IIc wherein:
A is a five or six membered heterocycle;
Z is chosen from $OR_1$, $NR_2R_3$, morpholine and optionally substituted piperazine;
$R_1$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_2$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;

$R_9$ is chosen from an alkyl group and $-(CH_2)_p-N(OH)C(O)R_{10}$;
p is an integer from 1 to 8;
$R_{10}$ is an alkyl group;
$R_{11}$ is chosen from hydrogen and alkyl.
In further embodiments, compounds have structural formula III:

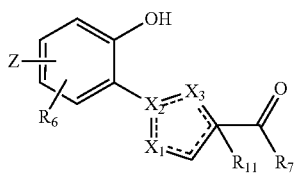

wherein:
  each dashed line represents a second bond which may be present or absent;
  $X_1$-$X_3$ are each chosen from $CR_{12}$, $NR_{13}$, O, and S, provided that when $X_3$ is N, $R_{13}$ is null, and $R_{11}$ is methyl or hydrogen, then $X_1$ is not S;
  Z is chosen from $OR_1$, $NR_2R_3$, morpholine and optionally substituted piperazine;
  $R_1$ is chosen from $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
  $R_2$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
  $R_3$ is chosen from hydrogen and alkyl; each m and each n is, independently, an integer from 1 to 8;
  x is an integer 0 to 8;
  y is an integer from 1 to 8;
  $R_4$ and $R_5$ are independently chosen from hydrogen, alkyl, and acyl;
  $R_6$ is chosen from hydrogen, alkyl and alkoxy;
  $R_7$ is chosen from $OR_8$ and $N(OH)R_9$;
  $R_8$ is chosen from hydrogen, alkyl and aralkyl;
  $R_9$ is chosen from an alkyl group and $-(CH_2)_p-N(OH)C(O)R_{10}$;
  p is an integer from 1 to 8;
  $R_{10}$ is an alkyl group;
  $R_{11}$ is chosen from hydrogen and alkyl.
  each $R_{12}$ is independently chosen from null, hydrogen, and lower alkyl; and
  each $R_{13}$ is independently chosen from null, hydrogen, and lower alkyl.
In further embodiments compounds have the structural formula III wherein:
  Z is $NR_2R_3$;
  $R_2$ is chosen from $[(CH_2)_m-O]_x-[(CH_2)_n-O]_y-R_4$, and $[(CH_2)_m-O]_x-[(CH_2)_n-NR_4]_y-R_5$; and
  $R_3$ is chosen from hydrogen and alkyl.
In other embodiments compounds have the structural formula III wherein Z is chosen from morpholine and optionally substituted piperazine.
In other embodiments compounds have the structural formula III wherein Z is $OR_1$.
In further embodiments compounds have the structural formula III wherein $R_1$ is $[(CH_2)_m-O]_x-[(CH_2)_n-O]_y-R_4$.
In further embodiments compounds have the structural formula III wherein:
  each m and each n is, independently, an integer from 1 to 4;
  x is an integer from 0 to 4; and
  y is an integer from 1 to 4.
In yet further embodiment compounds have the structural formula III wherein $R_4$ is alkyl.
In yet further embodiment compounds have the structural formula III wherein $R_4$ is methyl.
In further embodiments compounds have the structural formula III wherein:
  each n is 2;
  x is 0;
  y is an integer from 2 to 3; and
  $R_4$ is methyl.
In further embodiments compounds have the structural formula III wherein $R_7$ is $OR_8$.
In yet further embodiments compounds have the structural formula III wherein $R_8$ is hydrogen.
In further embodiments, compounds have structural formula chosen from IIIa, IIIb, IIIc and IIId:

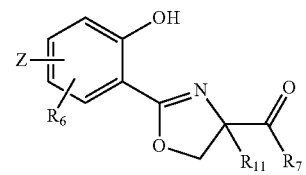

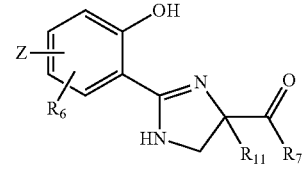

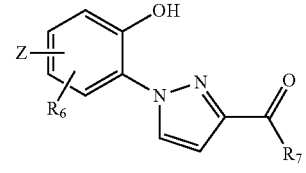

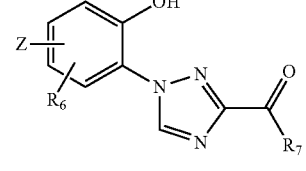

wherein all groups are as defined for Formula III.
In further embodiments, compounds have structural formula chosen from IIIa1, IIIa2, IIIa3, IIIb1, IIIb2, IIIb3, IIIc1, IIIc2, IIIc3, IIId1, IIId2, and IIId3:

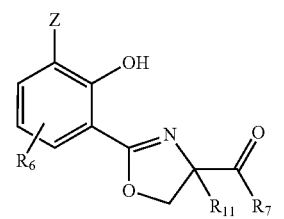

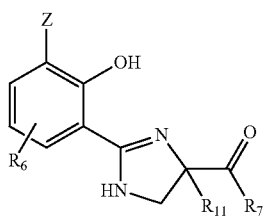
IIIa2
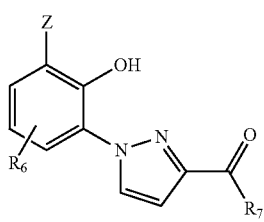
IIIa3
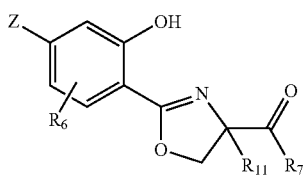
IIIb1
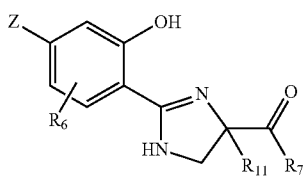
IIIb2
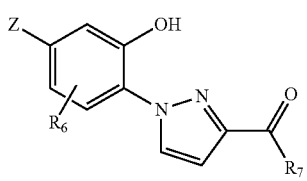
IIIb3
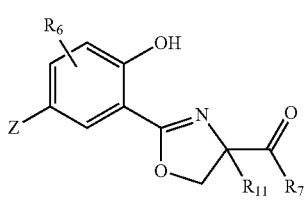
IIIc1
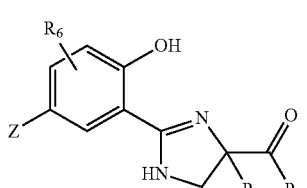
IIIc2
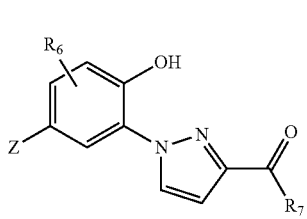
IIIc3
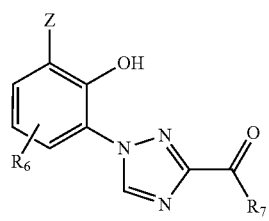
IIId1
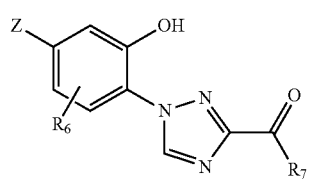
IIId2
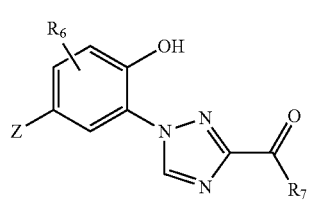
IIId3
wherein all groups are as defined for Formula III.
In certain embodiments, the compound is the (S) enantiomer at $OR_7$.
In certain embodiments, the compound is the (R) enantiomer at $OR_7$.
In further embodiments, compound has a structural formula chosen from
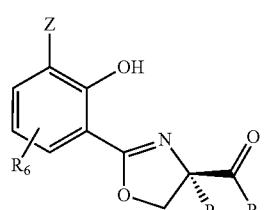
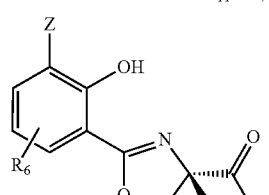
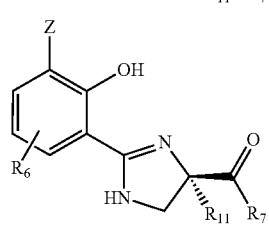

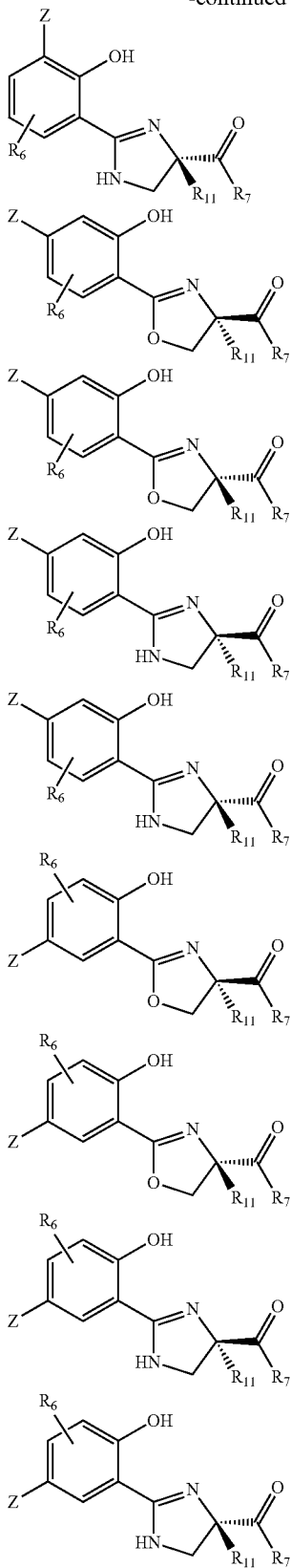

wherein all groups are as defined for Formula III.

In further embodiments compounds have the structural formula III wherein Z is $OR_1$.

In further embodiments compounds have the structural formula III wherein $R_1$ is $[(CH_2)_m—O]_x—[(CH_2)_n—O]_y—R_4$.

In further embodiments compounds have the structural formula III wherein:
each n is, independently, an integer from 1 to 4;
x is an integer from 0 to 4; and
y is an integer from 1 to 4.

In yet further embodiment compounds have the structural formula III wherein $R_4$ is alkyl.

In yet further embodiment compounds have the structural formula III wherein $R_4$ is methyl.

In further embodiments compounds have the structural formula III wherein:
each n is 2;
x is 0;
y is an integer from 2 to 3; and
$R_4$ is methyl.

In further embodiments compounds have the structural formula III wherein $R_7$ is $OR_8$.

In yet further embodiments compounds have the structural formula III wherein $R_8$ is hydrogen.

In further embodiments, compounds have structural formula IV:

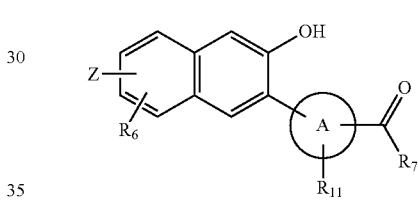

wherein:
A is a five or six membered heterocycle;
Z is chosen from $OR_1$, $NR_2R_3$, morpholine and optionally substituted piperazine;
$R_1$ is chosen from hydrogen, alkyl, $[(CH_2)_m—O]_x—[(CH_2)_n—O]_y—R_4$, $[(CH_2)_m—NH]_x—[(CH_2)_n—NR_4]_y—R_5$, and $[(CH_2)_m—O]_x—[(CH_2)_n—NR_4]_y—R_5$;
$R_2$ is chosen from hydrogen, alkyl, $[(CH_2)_m—O]_x—[(CH_2)_n—O]_y—R_4$, $[(CH_2)_m—NH]_x—[(CH_2)_n—NR_4]_y—R_5$, and $[(CH_2)_m—O]_x—[(CH_2)_n—NR_4]_y—R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $—(CH_2)_p—N(OH)C(O)R_{10}$;
p is an integer from 1 to 8;
$R_{10}$ is an alkyl group;
$R_{11}$ is chosen from hydrogen and alkyl.

In further embodiments compounds have the structural formula IV wherein A is a five membered heterocycle.

In certain embodiments, A has the structural formula

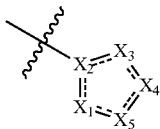

wherein:
each dashed line represents a second bond which may be present or absent;
$X_1$-$X_5$ are each chosen from $CR_{12}$, $NR_{13}$, O, and S, and no more than three of $X_1$-$X_5$ are heteroatoms;
each $R_{12}$ is independently chosen from null, hydrogen, and lower alkyl; and
each $R_{13}$ is independently chosen from null, hydrogen, and lower alkyl.

In further embodiments compounds have the structural formula V wherein $R_{11}$ is methyl.

In further embodiments compounds have the structural formula IV wherein:
Z is $NR_2R_3$;
$R_2$ is chosen from $[(CH_2)_m—O]_x—[(CH_2)_n—O]_y—R_4$, and $[(CH_2)_n—O]_x—[(CH_2)_m—NR_4]_y—R_5$; and
$R_3$ is chosen from hydrogen and alkyl.

In other embodiments compounds have the structural formula IV wherein Z is chosen from morpholine and optionally substituted piperazine.

In further embodiments compounds have the structural formula IV wherein Z is $OR_1$.

In further embodiments compounds have the structural formula IV wherein $R_1$ is $[(CH_2)_m—O]_x—[(CH_2)_n—O]_y—R_4$.

In further embodiments compounds have the structural formula IV wherein
each n is, independently, an integer from 1 to 4;
x is an integer from 0 to 4; and
y is an integer from 1 to 4.

In yet further embodiment compounds have the structural formula IV wherein $R_4$ is alkyl.

In further embodiments compounds have the structural formula IV wherein $R_7$ is $OR_8$.

In yet further embodiments compounds have the structural formula IV wherein $R_8$ is hydrogen.

In further embodiments, compounds have structural formula V:

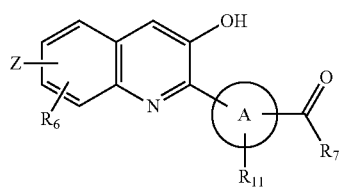

wherein:
A is a five or six membered heterocycle;
Z is chosen from $OR_1$, $NR_2R_3$, morpholine and optionally substituted piperazine;
$R_1$ is chosen from hydrogen, alkyl, $[(CH_2)_m—O]_x—[(CH_2)_n—O]_y—R_4$, $[(CH_2)_m—NH]_x—[(CH_2)_n—NR_4]_y—R_5$, and $[(CH_2)_m—O]_x—[(CH_2)_n—NR_4]_y—R_5$;
$R_2$ is chosen from hydrogen, alkyl, $[(CH_2)_m—O]_x—[(CH_2)_n—O]_y—R_4$, $[(CH_2)_m—NH]_x—[(CH_2)_n—NR_4]_y—R_5$, and $[(CH_2)_m—O]_x—[(CH_2)_n—NR_4]_y—R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and —$(CH_2)_p$—N(OH)C(O)$R_{10}$;
p is an integer from 1 to 8;
$R_{10}$ is an alkyl group;
$R_{11}$ is chosen from hydrogen and alkyl.

In further embodiments compounds have the structural formula V wherein A is a five membered heterocycle.

In certain embodiments, A has the structural formula

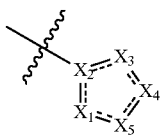

wherein:
each dashed line represents a second bond which may be present or absent;
$X_1$-$X_5$ are each chosen from $CR_{12}$, $NR_{13}$, O, and S, and no more than three of $X_1$-$X_5$ are heteroatoms;
each $R_{12}$ is independently chosen from null, hydrogen, and lower alkyl; and
each $R_{13}$ is independently chosen from null, hydrogen, and lower alkyl.

In further embodiments compounds have the structural formula V wherein $R_{11}$ is methyl.

In further embodiments compounds have the structural formula V wherein:
Z is $NR_2R_3$;
$R_2$ is chosen from $[(CH_2)_m—O]_x—[(CH_2)_n—O]_y—R_4$, and $[(CH_2)_n—O]_x—[(CH_2)_m—NR_4]_y—R_5$; and
$R_3$ is chosen from hydrogen and alkyl.

In other embodiments compounds have the structural formula V wherein Z is chosen from morpholine and optionally substituted piperazine.

In further embodiments compounds have the structural formula V wherein Z is $OR_1$.

In further embodiments compounds have the structural formula V wherein $R_1$ is $[(CH_2)_n—O]_x—[(CH_2)_n—O]_y—R_4$.

In further embodiments compounds have the structural formula V wherein each n is, independently, an integer from 1 to 4; x is an integer from 0 to 4; and y is an integer from 1 to 4.

In yet further embodiment compounds have the structural formula V wherein $R_4$ is alkyl.

In further embodiments compounds have the structural formula V wherein $R_7$ is $OR_8$.

In yet further embodiments compounds have the structural formula V wherein $R_8$ is hydrogen.

In further embodiments, compounds have structural formula VI:

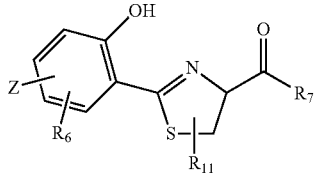

VI wherein:
Z is chosen from $OR_1$, $NR_2R_3$, morpholine and optionally substituted piperazine;
$R_1$ is chosen from hydrogen, alkyl, $[(CH_2)_m\text{—O}]_x\text{—}[(CH_2)_n\text{—O}]_y\text{—}R_4$, $[(CH_2)_m\text{—NH}]_x\text{—}[(CH_2)_n\text{—}NR_4]_y\text{—}R_5$, and $[(CH_2)_m\text{—O}]_x\text{—}[(CH_2)_n\text{—}NR_4]_y\text{—}R_5$;
$R_2$ is chosen from hydrogen, alkyl, $[(CH_2)_m\text{—O}]_x\text{—}[(CH_2)_n\text{—O}]_y\text{—}R_4$, $[(CH_2)_m\text{—NH}]_x\text{—}[(CH_2)_n\text{—}NR_4]_y\text{—}R_5$, and $[(CH_2)_m\text{—O}]_x\text{—}[(CH_2)_n\text{—}NR_4]_y\text{—}R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $\text{—}(CH_2)_p\text{—}N(OH)C(O)R_{10}$;
p is an integer from 1 to 8;
$R_{10}$ is an alkyl group;
$R_{11}$ is chosen from hydrogen and alkyl.

In certain embodiments,
$R_{11}$ is hydrogen; and
$R_1$ is chosen from hydrogen, $C_2$-$C_6$ alkyl, $[(CH_2)_m\text{—O}]_x\text{—}[(CH_2)_n\text{—O}]_y\text{—}R_4$, and $[(CH_2)_m\text{—O}]_x\text{—}[(CH_2)_n\text{—}NR_4]_y\text{—}R_5$.

In further embodiments compounds have the structural formula VI wherein:
Z is $NR_2R_3$;
$R_2$ is chosen from $[(CH_2)_m\text{—O}]_x\text{—}[(CH_2)_n\text{—O}]_y\text{—}R_4$, and $[(CH_2)_n\text{—O}]_x\text{—}[(CH_2)_m\text{—}NR_4]_y\text{—}R_5$; and
$R_3$ is chosen from hydrogen and alkyl.

In other embodiments compounds have the structural formula VI wherein Z is chosen from morpholine and optionally substituted piperazine.

In further embodiments compounds have the structural formula VI wherein Z is $OR_1$.

In further embodiments compounds have the structural formula VI wherein $R_7$ is $OR_8$.

In another embodiment compounds have the structural formula VI, wherein $R_8$ is hydrogen.

In further embodiments compounds have structural formula $VI_1$

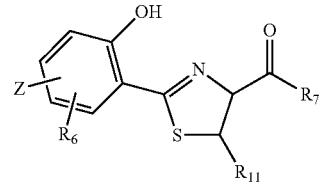

$VI_1$ wherein:
Z is chosen from $OR_1$, $NR_2R_3$, morpholine and optionally substituted piperazine;
$R_1$ is chosen from $[(CH_2)_m\text{—O}]_x\text{—}[(CH_2)_n\text{—O}]_y\text{—}R_4$, $[(CH_2)_m\text{—NH}]_x\text{—}[(CH_2)_n\text{—}NR_4]_y\text{—}R_5$, and $[(CH_2)_n\text{—O}]_x\text{—}[(CH_2)_m\text{—}NR_4]_y\text{—}R_5$;
$R_2$ is chosen from hydrogen, alkyl, $[(CH_2)_m\text{—O}]_x\text{—}[(CH_2)_n\text{—O}]_y\text{—}R_4$, $[(CH_2)_m\text{—NH}]_x\text{—}[(CH_2)_n\text{—}NR_4]_y\text{—}R_5$, and $[(CH_2)_m\text{—O}]_x\text{—}[(CH_2)_n\text{—}NR_4]_y\text{—}R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $\text{—}(CH_2)_p\text{—}N(OH)C(O)R_{10}$;
p is an integer from 1 to 8;
$R_{10}$ is an alkyl group;
$R_{11}$ is alkyl.

In further embodiments, compounds have structural formula $VI_2$:

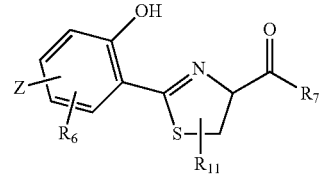

$VI_2$ wherein:
Z is chosen from $NR_2R_3$, morpholine and optionally substituted piperazine;
$R_2$ is chosen from hydrogen, alkyl, $[(CH_2)_m\text{—O}]_x\text{—}[(CH_2)_n\text{—O}]_y\text{—}R_4$, $[(CH_2)_m\text{—NH}]_x\text{—}[(CH_2)_n\text{—}NR_4]_y\text{—}R_5$, and $[(CH_2)_m\text{—O}]_x\text{—}[(CH_2)_n\text{—}NR_4]_y\text{—}R_5$;
$R_3$ is chosen from hydrogen and alkyl;
each m and each n is, independently, an integer from 1 to 8;
x is an integer 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $\text{—}(CH_2)_p\text{—}N(OH)C(O)R_{10}$;
p is an integer from 1 to 8;
$R_{10}$ is an alkyl group;
$R_{11}$ is chosen from hydrogen and alkyl.

In further embodiments, compounds have structural formula VIa, VIb, or VIc:

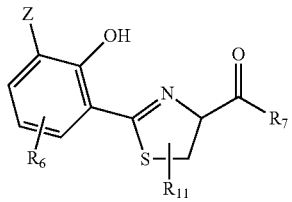

VIa

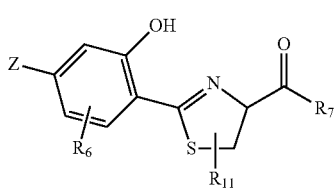

VIb

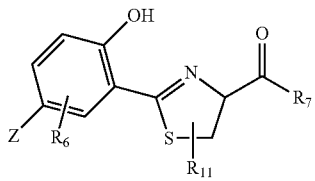

VIc wherein:
- Z is chosen from $OR_1$, $NR_2R_3$, morpholine and optionally substituted piperazine;
- $R_1$ is chosen from hydrogen, alkyl, $[(CH_2)_m—O]_x—[(CH_2)_n—O]_y—R_4$, and $[(CH_2)_m—O]_x—[(CH_2)_n—NR_4]_y—R_5$;
- $R_2$ is chosen from hydrogen, alkyl, $[(CH_2)_m—O]_x—[(CH_2)_n—O]_y—R_4$, and $[(CH_2)_m—O]_x—[(CH_2)_n—NR_4]_y—R_5$;
- $R_3$ is chosen from hydrogen and alkyl;
- each m and each n is, independently, an integer from 1 to 8;
- x is an integer 0 to 8;
- y is an integer from 1 to 8;
- $R_4$ and $R_5$ are independently chosen from hydrogen, alkyl, and acyl;
- $R_6$ is chosen from hydrogen, alkyl and alkoxy;
- $R_7$ is chosen from $OR_8$ and $N(OH)R_9$;
- $R_8$ is chosen from hydrogen, alkyl and aralkyl;
- $R_9$ is chosen from an alkyl group and $—(CH_2)_p—N(OH)C(O)R_{10}$;
- p is an integer from 1 to 8;
- $R_{10}$ is an alkyl group;
- $R_{11}$ is chosen from hydrogen and alkyl.

In certain embodiments, the compound is the (S) enantiomer at $OR_7$.

In certain embodiments, the compound is the (R) enantiomer at $OR_7$.

In further embodiments, compounds have structural formula chosen from

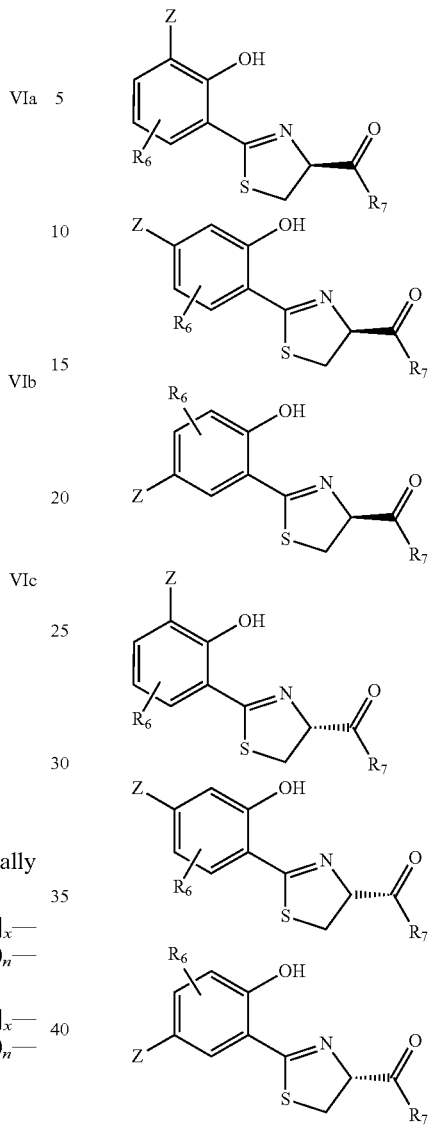

wherein all groups are as defined for Formula VI.

In certain embodiments of the present invention are provided pharmaceutical compositions comprising the compounds as disclosed herein together with at least one pharmaceutically acceptable excipient.

In certain embodiments of the present invention are provided a method of treating a metal-mediated condition in a subject comprising administering to the subject a therapeutically effective amount of a prodrug as disclosed herein.

In further embodiments, said metal is trivalent.

In further embodiments, said metal is iron.

In further embodiments, said condition is iron overload.

In further embodiments, said condition is the result of mal-distribution or redistribution of iron in the body.

In further embodiments, said condition is chosen from atransferrinemia, aceruloplasminemia, and Fredreich's ataxia.

In further embodiments, said condition is the result of transfusional iron overload.

In further embodiments, said condition is chosen from beta-thalassemia major and intermedia, sickle cell anemia, Diamond-Blackfan anemia, sideroblastic anemia, chronic hemolytic anemias, off-therapy leukemias, bone marrow transplant and myelodysplastic syndrome.

In further embodiments, said condition is a hereditary condition resulting in the excess absorption of dietary iron.

In further embodiments, said condition is chosen from hereditary hemochromatosis and porphyria cutanea tarda.

In further embodiments, said condition is diabetes.

In further embodiments, said condition is an acquired disease that results in excess dietary iron absorption.

In further embodiments, said condition is a liver disease.

In further embodiments, said disease is hepatitis.

In further embodiments, said condition is lanthanide or actinide overload.

In further embodiments, the therapeutically effective amount of a compound as disclosed herein that induces the bodily excretion of iron or other trivalent metal is greater than 0.2 mg/kg/d in the subject.

In further embodiments, the therapeutically effective amount of a compound as disclosed herein can be given at a dose of at least 10 mg/kg/d without clinically apparent toxic effects on the kidney, bone marrow, thymus, liver, spleen, heart or adrenal glands.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), —C=::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C—:::C—, —CC—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR, wherein R and R are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The terms "benzo" and "benz," as used herein, alone or in combination, refer to the divalent group C$_6$H$_4$=derived from benzene. Examples include benzothiophene and benzimidazole.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said heterocycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The term "hydroxyalkyl," as used herein, alone or in combination, refers to a hydroxy group attached to the parent molecular moiety through an alkyl group.

The phrase "in the main chain" refers to the longest contiguous or adjacent chain of carbon atoms starting at the point of attachment of a group to the compounds of any one of the formulas disclosed herein.

The term "lower," as used herein, alone or in a combination, where not otherwise specifically defined, means containing from 1 to and including 6 carbon atoms.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, ester, acyl, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

Diseases to be treated by the methods disclosed herein include metal-mediated conditions. As used herein, a "metal-mediated condition" is one in which metal ions (either in imbalance, excess relative or absolute, mal-distribution, etc.) play a role in pathogenesis of the disease or its symptoms. Metal-mediated conditions include conditions responsive to chelation, sequestration, or elimination of metals, such as iron overload, lanthanide overload, and actinide overload. Other disease involving metals that could be treated include those in which the metal is vital for the survival of an organism requiring the metal. Thus, chelation of iron can be used as a treatment for malaria, an intracellular parasite that requires iron to replicate and cause infection.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "chelation" as used herein means to coordinate (as in a metal ion) with and inactivate. Chelation also includes decorporation, a term which itself encompasses chelation and excretion.

The term "iron-clearing efficiency (ICE)" as used herein refers to the efficaciousness of a given concentration of chelator in clearing iron from the body or one of its organs or parts. Efficaciousness in turn concerns quantity of iron removed from a target system (which may be a whole body, an organ, or other) in a unit of time. Chelators are needed for three clinical situations: for acute iron toxicity from ingestion or infusion of iron; to reduce total body iron secondary to transfusion or excess iron absorption; for maintenance of iron balance after total body iron has been satisfactorily reduces and only daily dietary iron needs to be excreted. In practical terms, therefore, for chronic iron overload secondary to transfusion, the recommendation is that between 0.3 and 0.5 mg Fe/kg body weight of the patient per day need be excreted. For the maintenance treatment, 0.25-1 mg/kg/d is sufficient.

The term "therapeutically acceptable" refers to those compounds (or salts, polymorphs, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium (e.g., NaOH), potassium (e.g., KOH), calcium (including $Ca(OH)_2$), magnesium (including $Mg(OH)_2$ and magnesium acetate), zinc, (including $Zn(OH)_2$ and zinc acetate) and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated.

In certain embodiments, the salts may include calcium, magnesium, potassium, sodium, zinc, and piperazine salts of compounds disclosed herein.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e. g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term "amorphous form," as used herein, refers to a noncrystalline form of a substance.

The term "solubility" is generally intended to be synonymous with the term "aqueous solubility," and refers to the ability, and the degree of the ability, of a compound to dissolve in water or an aqueous solvent or buffer, as might be found under physiological conditions. Aqueous solubility is, in and of itself, a useful quantitative measure, but it has additional utility as a correlate and predictor, with some limitations which will be clear to those of skill in the art, of oral bioavailability. In practice, a soluble compound is generally desirable, and the more soluble, the better. There are notable exceptions; for example, certain compounds intended to be administered as depot injections, if stable over time, may actually benefit from low solubility, as this may assist in slow release from the injection site into the plasma. Solubility is typically reported in mg/mL, but other measures, such as g/g, may be used. Solubilities typically deemed acceptable may range from 1 mg/mL into the hundreds or thousands of mg/mL.

While it may be possible for the compounds and prodrugs disclosed herein to be administered as the raw chemical, it is also possible to present them as a pharmaceutical formulation. Accordingly, provided herein are pharmaceutical formulations which comprise one or more of certain compounds and prodrugs disclosed herein, or one or more pharmaceutically acceptable salts, esters, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds and prodrugs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and prodrugs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds and prodrugs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds and prodrugs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and prodrugs to allow for the preparation of highly concentrated solutions.

In addition to the formulations described previously, a compound or prodrug as disclosed herein may also be formulated as a depot preparation. Such long acting formulations may be administered by implantation (for example subcutaneously or intramuscularly) or by intramuscular injection. Thus, for example, the compounds and prodrugs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds and prodrugs may also be formulated in rectal compositions such as suppositories or retention enemas, e.g., containing conventional suppository bases such as cocoa butter, polyethylene glycol, or other glycerides.

Certain compounds and prodrugs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds and prodrugs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds and prodrugs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, $2^{nd}$, J Neuroimmune Pharmacol. 2007 March; 2(1):81-6. Epub 2006 Sep. 15.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds and prodrugs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compound or prodrug which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds and prodrugs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds and prodrugs described herein (or a pharmaceutically acceptable salt or ester thereof) in combination with another therapeutic agent. By way of example only, if one of the side effects experienced by a patient upon receiving one of the compounds herein for the treatment of actinide poisoning is depletion of essential trace minerals required by the body for proper functioning, then it may be appropriate to administer a strong chelating agent in combination with supplements of essential trace minerals required by the body for proper functioning, for example zinc and magnesium, to replace those which will inadvertently be lost to chelation therapy. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for thalassemia involving administration of one of the compounds described herein, increased therapeutic benefit may result by also providing the patient with another therapeutic agent for thalassemis, for example deferoxamine. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: deferasirox, deferiprone, deferoxamine, DTPA (diethylene triamine pentaacetic acid), EGTA (ethylene glycol tetraacetic acid), EDTA (ethylenediamine tetraacetic acid), DMSA (dimercaptosuccinic acid), DMPS (dimercapto-propane sulfonate), BAL (dimercaprol), BAPTA (aminophenoxyethane-tetraacetic acid), D-penicillamine, and alpha lipoic acid.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating disorders and symptoms relating to metal toxicity in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of disorders and symptoms relating to metal toxicity.

Specific diseases to be treated by the compounds, compositions, and methods disclosed herein include iron overload or mal-distribution or redistribution of iron in the body such as atransferrinemia, aceruloplasminemia, or Fredreich's ataxia; transfusional iron overload such as with beta-thalassemia major and intermedia, sickle cell anemia, Diamond-Blackfan anemia, sideroblastic anemia, chronic hemolytic anemias, off-therapy leukemias, bone marrow transplant or myelodysplastic syndrome; a hereditary condition resulting in the excess absorption of dietary iron such as hereditary hemochromatosis, or porphyria cutanea tarda; an acquired disease that results in excess dietary iron absorption such as hepatitis; other liver diseases; heart disease, cardiovascular disease, and related conditions, including cardiomyopathy, coronary heart disease, inflammatory heart disease, ischemic heart disease, valvular heart disease, hypertensive heart disease, and atherosclerosis; iron, lanthanide or actinide acute poisoning or chronic overload; infectious agents that can be controlled by iron deprivation.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference

GENERAL SYNTHETIC METHODS FOR PREPARING COMPOUNDS

Certain compounds of the invention can be synthesized as described in Bergeron, R J et al., "Design, Synthesis, and Testing of Non-Nephrotoxic Desazadesferrithiocin Polyether Analogues," *J Med Chem.* 2008, 51(13), 3913-23.

The following schemes can generally be used to practice the present invention.

In Schemes 1-5 below, n denotes the length of the polyether chain in ethoxy units and can generally be an integer from 1 to 8. In certain embodiments, n is 2 to 3.

Scheme 1

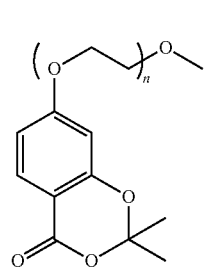

3N HCl, dioxane
60° C., 2 h

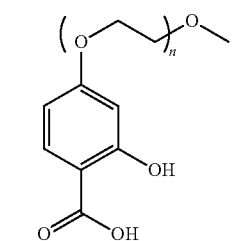

1) (COCl)₂, DMF, DCM, 0° C.~r.t., 3 h
TFA H₂N CH₃
HO
CO₂Bn
2) Et₃N, DCM, 0~r.t., 3 h

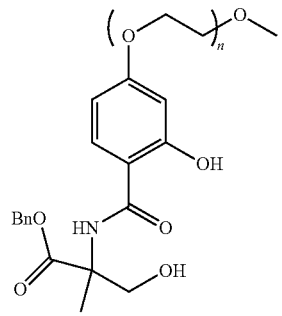

PSBSF, DMAP, DCM
r.t., 3 h

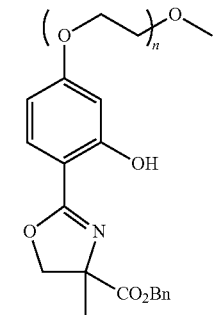

H2, Pd/C, MeOH
r.t., overnight

Scheme 2

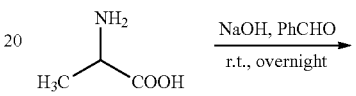

NaOH, PhCHO
r.t., overnight

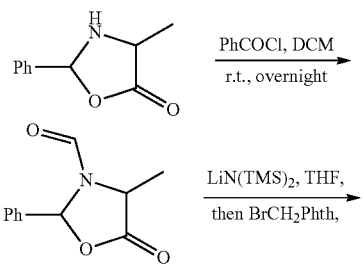

PhCOCl, DCM
r.t., overnight

LiN(TMS)₂, THF,
then BrCH₂Phth,

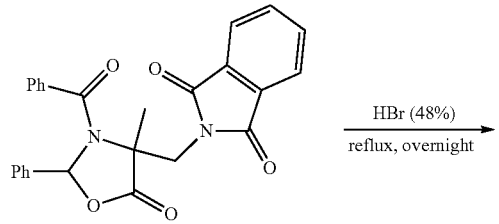

HBr (48%)
reflux, overnight

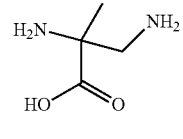

2HBr salt

SOCl₂, MeOH
reflux, overnight

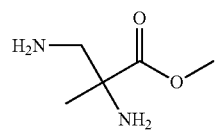

2HCl salt

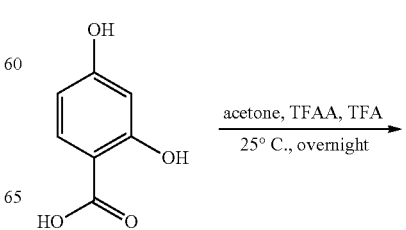

acetone, TFAA, TFA
25° C., overnight

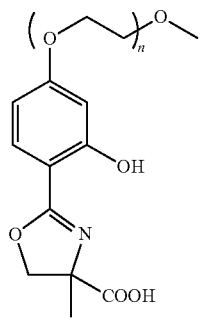

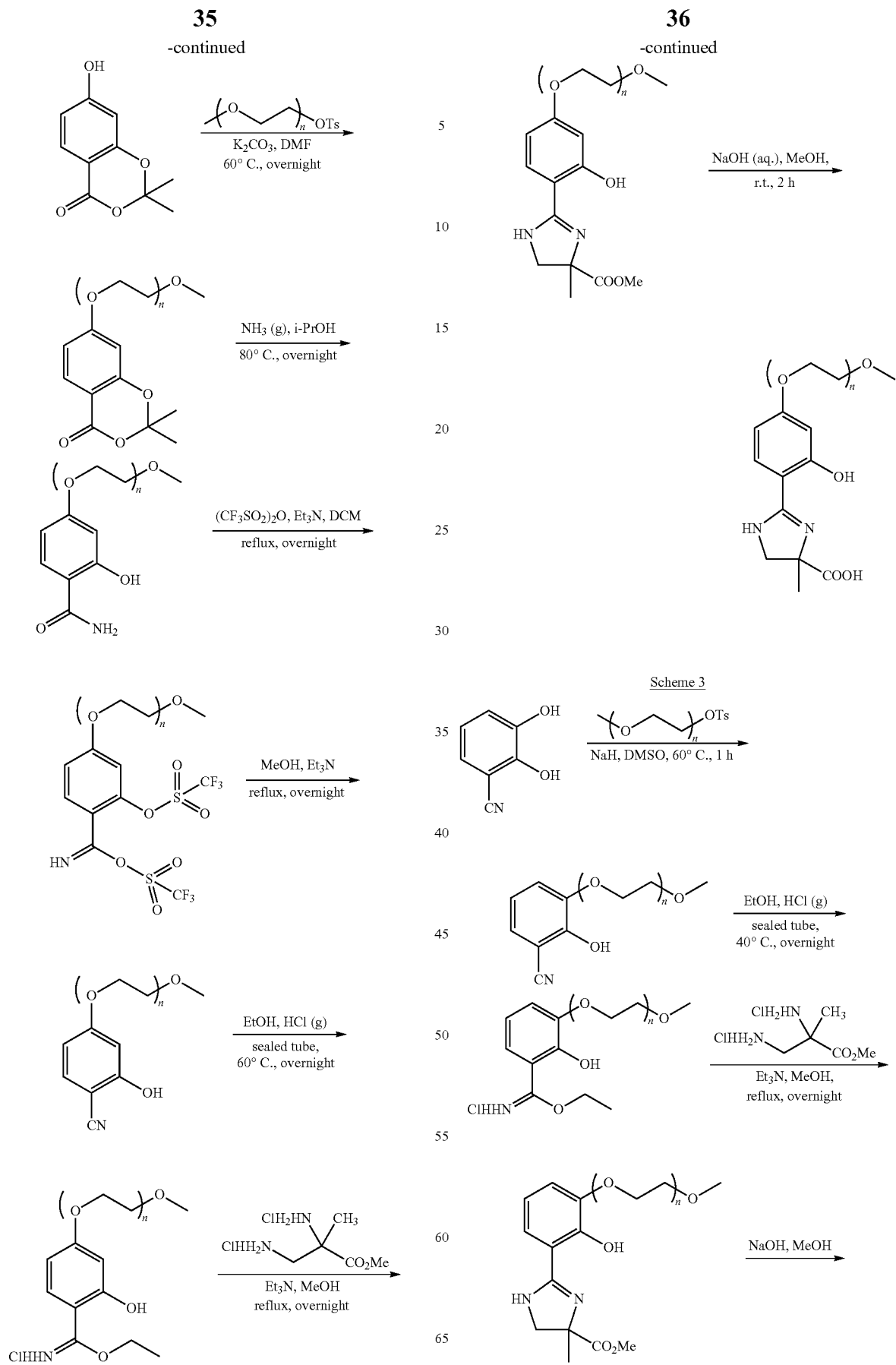

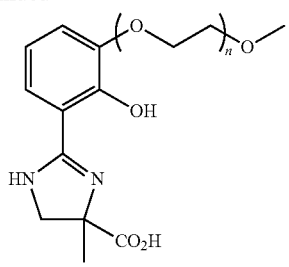

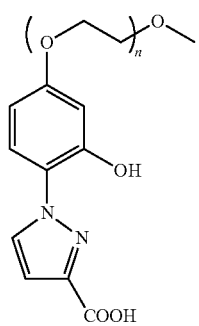

Scheme 4

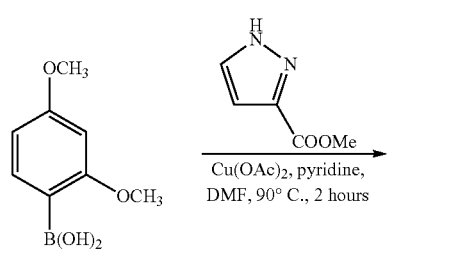

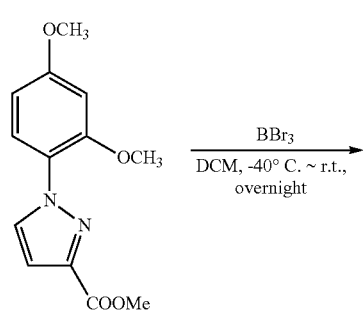

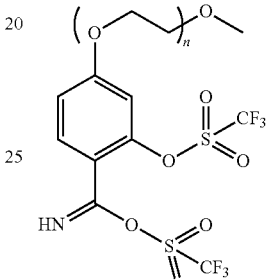

Scheme 5

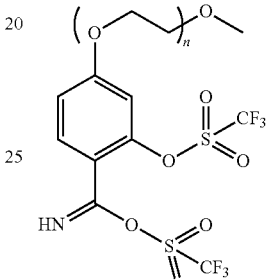

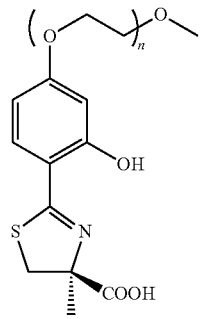

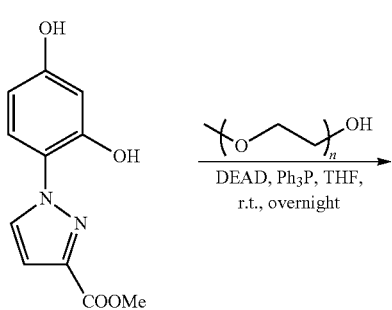

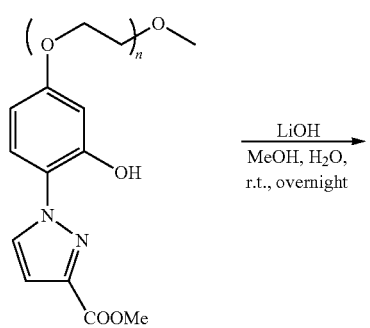

In Schemes 6-7 below, RX generally represents a polyether or polyamine chain which substitutes the core through a heteroatom. Generally, the R polyether or polyamine comprises repeating units of alkoxy or alkylamino units (for example, ethoxy or propylamino units), and the heteroatom X is chosen from O, S, and N. R' and R" are generally each independently optionally substituted alkyl or hydrogen. In certain embodiments, R is a polyether chain of 1 to 8 ethoxy units the core-distal end of which terminates in $CH_3$—, X is O, and R' is lower alkyl or hydrogen. In further embodiments, the R polyether chain is of 2 to 3 ethoxy units and R' and R" are each independently methyl or hydrogen.

Scheme 1

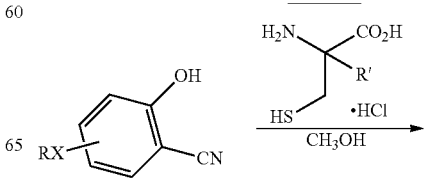

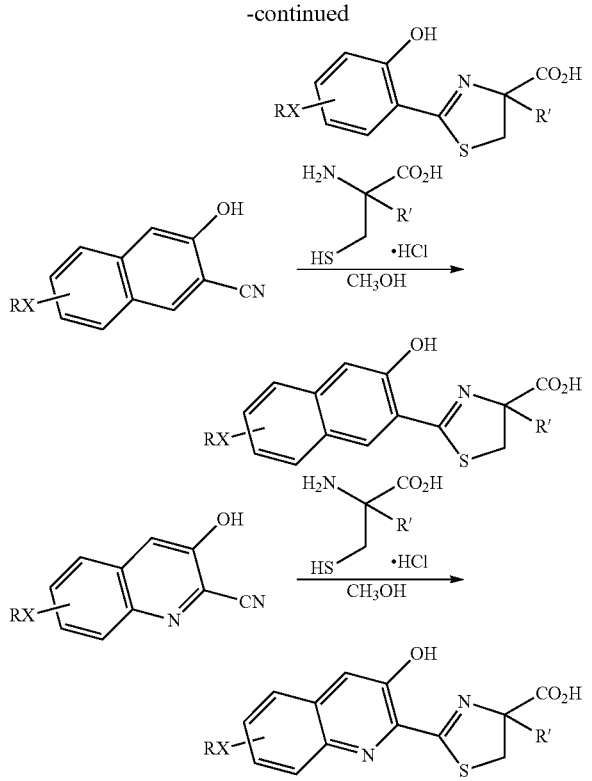
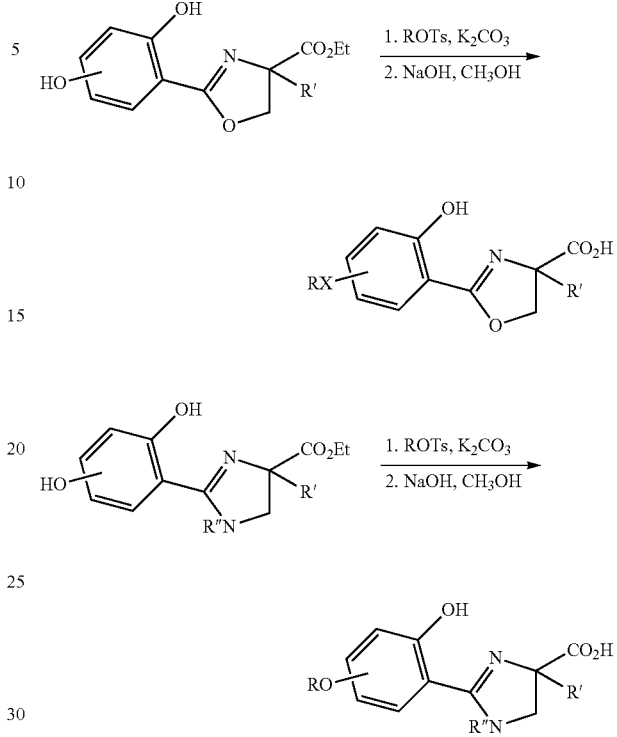
Scheme 3
Scheme 2
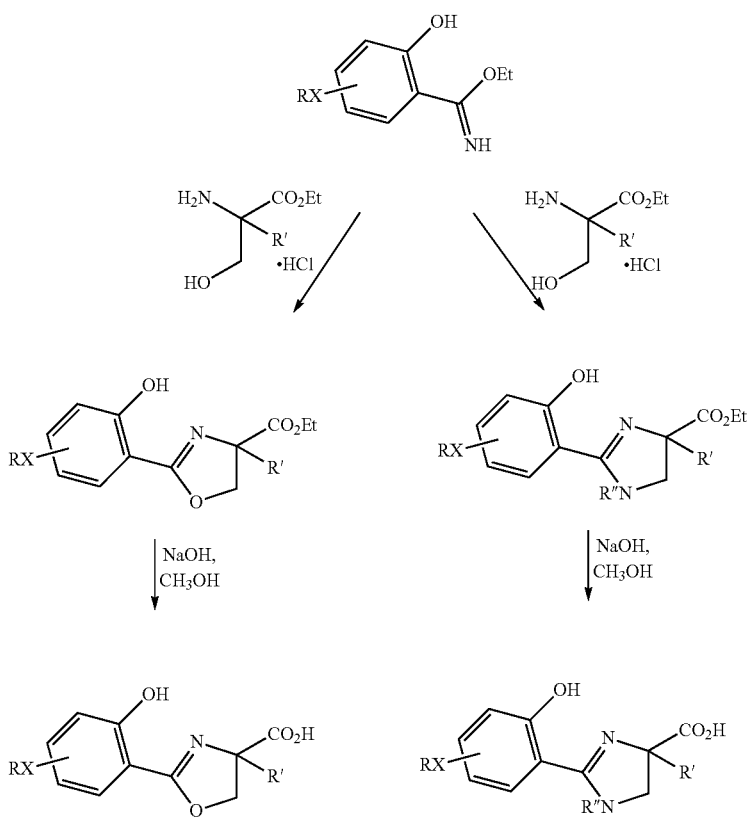

The invention is further illustrated by the following examples. Examples A-F have been previously disclosed in the art.

EXAMPLE A (S)-2-(2-hydroxy-4-(2-(2-methoxyethoxy)ethoxy) phenyl)-4-methyl-4,5-dihydrothiazole-4-carboxylic acid

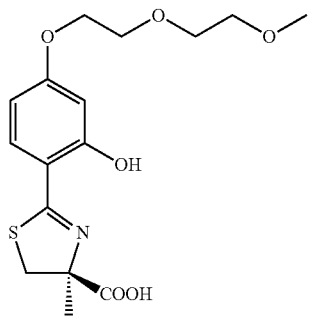 [SMILES: COCCOCCOc1ccc(C2=N[C@@](C)(C(=O)O)CS2)c(O)c1]

Step 1

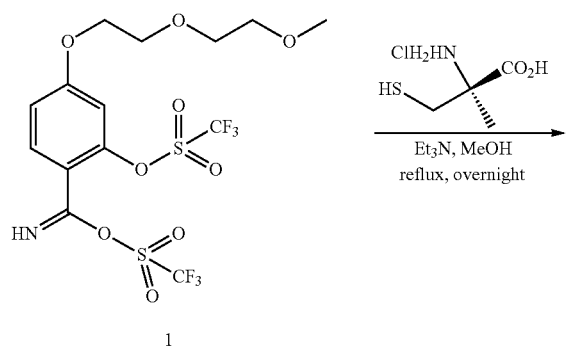

(S)-2-(2-hydroxy-4-(2-(2-methoxyethoxy)ethoxy) phenyl)-4-methyl-4,5-dihydrothiazole-4-carboxylic acid To a solution of trifluoromethanesulfonic 4-(2-(2-methoxyethoxy)ethoxy)-2-(trifluoromethylsulfonyloxy)benzimidic anhydride (0.5 g, crude, ~1 mmol) in MeOH (10 mL) was added (S)-2-(chloroamino)-3-mercapto-2-methylpropanoic acid (0.24 g, crude, ~1.0 mmol), then $Et_3N$ (2 mL) was added dropwise at 0° C. The resulting solution was refluxed overnight. The solvent was evaporated under vacuum and the residue was purified by prep-HPLC to obtain the title compound as colorless oil (100 mg). $^1$H NMR (300 MHz, $CD_3OD$, n=2): δ 7.55-7.60 (m, 1H), 6.55-6.60 (m, 2H), 4.05-4.20 (m, 2H), 3.85-4.05 (m, 1H), 3.75-3.85 (m, 2H), 3.60-3.70 (m, 2H), 3.45-3.60 (m, 3H), 3.33 (s, 3H), 1.80 (s, 3H). LC-MS (ES, m/z): 356 $[M+H]^+$.

Example A has been previously made and tested; see, e.g., US2008/0214630A1 Tables 1 and 2.

EXAMPLE B (S)-2-(2-hydroxy-4-(2-(2-(2-methoxyethoxy)ethoxy) ethoxy)phenyl)-4-methyl-4,5-dihydrothiazole-4-carboxylic acid

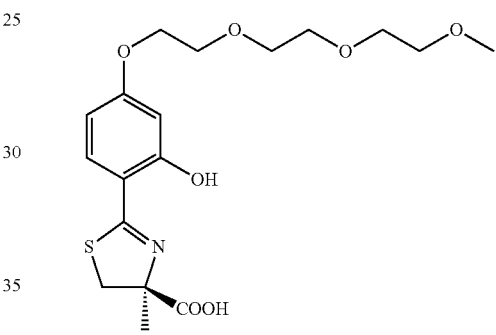

Example B was prepared as described in Example A using trifluoromethanesulfonic 4-(2-(2-(2-methoxyethoxy)ethoxy)ethoxy)-2-(trifluoromethylsulfonyloxy)benzimidic anhydride as a starting material. $^1$H NMR (300 MHz, $CD_3OD$, n=3): δ 7.55-7.60 (m, 1H), 6.55-6.60 (m, 2H), 4.05-4.20 (m, 2H), 3.80-4.05 (m, 3H), 3.40-3.80 (m, 9H), 3.23 (s, 3H), 1.77 (s, 3H). LC-MS (ES, m/z): 400 $[M+H]^+$.

Example B has been previously made and tested; see, e.g., Bergeron, R. J. et al, *Biometals* 2011 April; 24(2):239-58 and WO2011/028255A2.

EXAMPLE C (S)-2-(4-(2,5,8,11-tetraoxatridecan-13-yloxy)-2-hydroxyphenyl)-4-methyl-4,5-dihydrothiazole-4-carboxylic acid

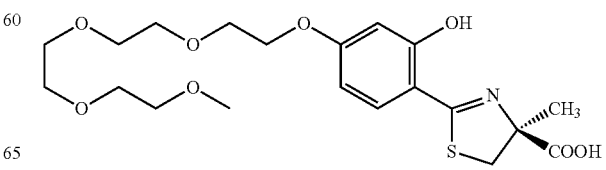

Example C has been previously made and tested; see, e.g., Bergeron, R. J. et al, *Biometals* 2011 April; 24(2):239-58 and WO2011/028255A2.

EXAMPLE D (S)-2-(2-hydroxy-3-(2-(2-methoxyethoxy)ethoxy) phenyl)-4-methyl-4,5-dihydrothiazole-4-carboxylic acid

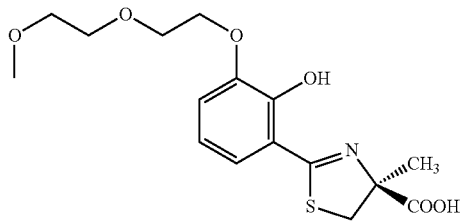 [SMILES: COCCOCCOc1cccc(C2=N[C@@](C)(C(=O)O)CS2)c1O]

Example D has been previously made and tested; see, e.g., Bergeron, R. J. et al, *Biometals* 2011 April; 24(2):239-58.

EXAMPLE E (S)-2-(2-hydroxy-3-(2-(2-(2-methoxyethoxy)ethoxy) ethoxy)phenyl)-4-methyl-4,5-dihydrothiazole-4-carboxylic acid

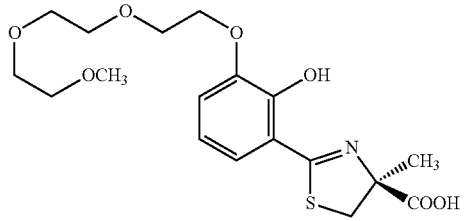 [SMILES: COCCOCCOCCOc1cccc(C2=N[C@@](C)(C(=O)O)CS2)c1O]

Example E has been previously made and tested; see, e.g., Bergeron, R. J. et al, *Biometals* 2011 April; 24(2):239-58 and US2008/093812A1.

EXAMPLE F (S)-2-(3-(2,5,8,11-tetraoxatridecan-13-yloxy)-2-hydroxyphenyl)-4-methyl-4,5-dihydrothiazole-4-carboxylic acid

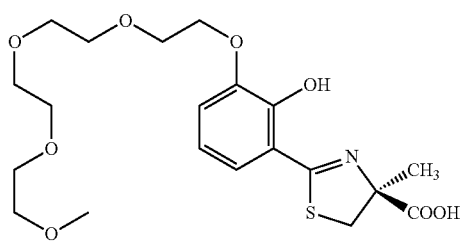 [SMILES: COCCOCCOCCOCCOc1cccc(C2=N[C@@](C)(C(=O)O)CS2)c1O]

Example F has been previously made and tested; see, e.g., Bergeron, R. J. et al, *Biometals* 2011 April; 24(2):239-58.

EXAMPLE 1

2-(2-hydroxy-4-(2-(2-methoxyethoxy)ethoxy)phenyl)-4-methyl-4,5-dihydrooxazole-4-carboxylic acid

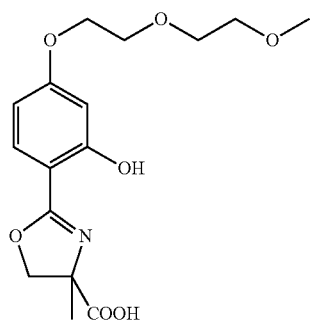 [SMILES: COCCOCCOc1ccc(C2=NC(C)(C(=O)O)CO2)c(O)c1]

Step 1

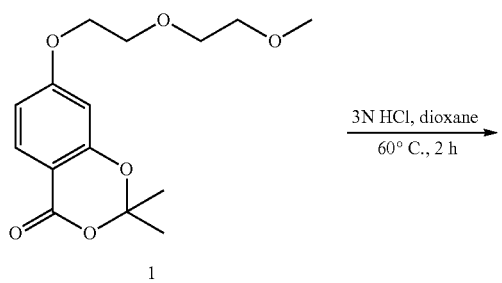

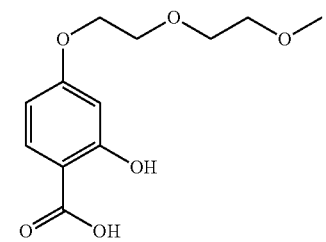

2-hydroxy-4-(2-(2-methoxyethoxy)ethoxy)benzoic acid

To a solution of 1 (1.5 g, 5.1 mmol) in dioxane (20 mL) was added 3N HCl (10 mL) and the mixture was stirred at 60° C. for 2 h. The solvent was removed under reduced pressure. This resulted in 1.3 g of the desired product 2 in white solid. LC-MS: m/z 257 (M+H$^+$)

Step 2

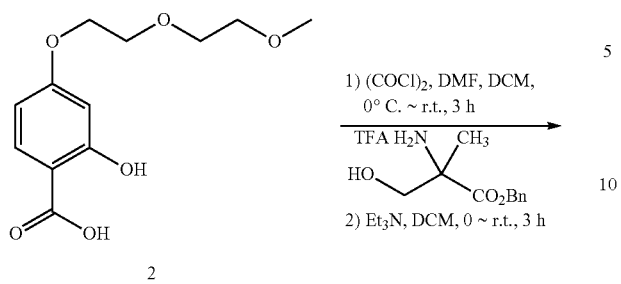

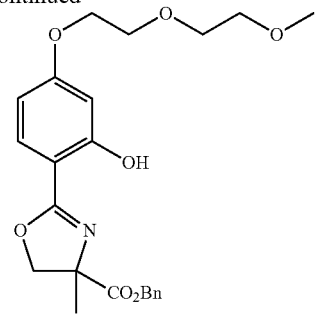

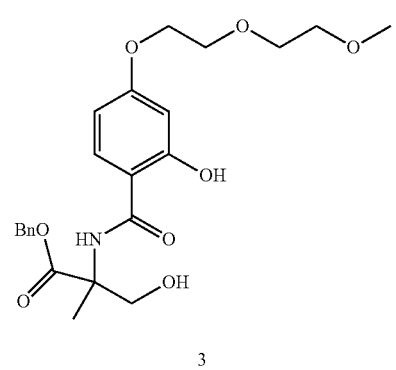

benzyl 3-hydroxy-2-(2-hydroxy-4-(2-(2-methoxy-ethoxy)ethoxy)benzamido)-2-methylropanoate To a solution of 2 (0.7 g, 2.7 mmol, 1.0 eq) in DCM (15 mL) was added oxalyl dichloride (1.7 g, 13.5 mmol, 5.0 eq) and one drop of DMF at 0° C. The resulting solution was stirred at room temperature for another 2 h. The volatile phase was removed under reduced pressure. The residue was dissolved in DCM (10 mL) and the resulting solution was added to a mixture of benzyl 2-amino-3-hydroxy-2-methylpropanoate (0.55 g. 2.7 mmol) and triethylamine (0.8 g, 8.1 mmol) in DCM at 0° C. The resulting mixture was stirred at room temperature overnight. The volatile phase was removed under reduced pressure. The residue was applied onto silica gel with PE/EA (1/1). This resulted 0.2 g of the desired product 3 in colorless oil. LC-MS: m/z 448 (M+H⁺).

Step 3

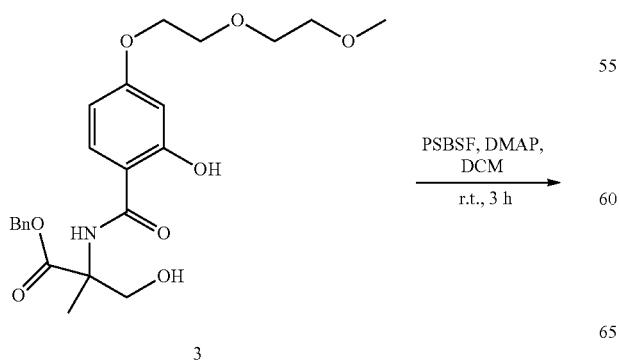

benzyl 2-(2-hydroxy-4-(2-(2-methoxyethoxy)ethoxy)phenyl)-4-methyl-4,5-dihydrooxazole-4-carboxylate To a solution of 3 (0.2 g, 0.45 mmol, 1.0 eq) and DMAP (0.16 g, 1.35 mmol, 3.0 eq) in DCM (15 mL) was added PSBSF (0.16 g, 5.4 mmol, 1.2 eq) dropwise at room temperature. The resulting solution was stirred at room temperature for another 2 h. The volatile phase was removed under reduced pressure. The residue was submitted to silica gel chromatography eluting with PE/EA (3/1). This resulted in 0.12 g of the desired product 4 as a colorless oil. LC-MS: m/z 448 (M+H⁺).

Step 4

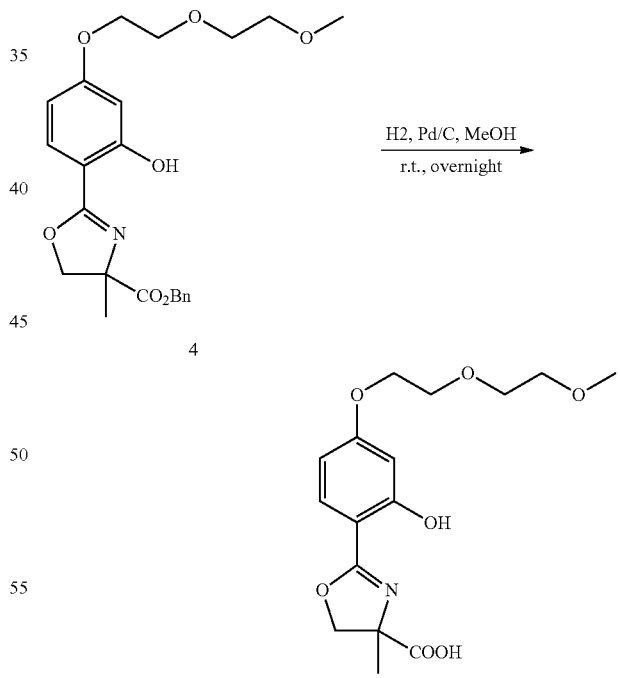

2-(2-hydroxy-4-(2-(2-methoxyethoxy)ethoxy)phenyl)-4-methyl-4,5-dihydrooxazole-4-carboxylic acid A solution of 4 (0.12 g, 0.28 mmol, 1.0 eq) and Pd/C (12 mg, 10%) in MeOH (15 mL) was stirred at room temperature under hydrogen atmosphere overnight. The solid was filtrated off and the filtrate was concentrated under vacuum. This resulted in 85 mg of 5 as a colorless semi-solid. $^1$H-NMR (300 MHz, DMSO-$d_6$, n=2): δ 1.26 (s, 3H), 3.27 (s, 3H), 3.48-3.49 (m, 2H), 3.59-3.60 (m, 2H), 3.74-3.75 (m, 2H), 4.14-4.15 (m, 2H), 4.24 (q, 1H, J=8.7 Hz), 4.75 (q, 1H, J=8.7 Hz), 6.55 (q, 1H, J=8.7 Hz), 6.57 (s, 1H), 7.54 (q, 1H, J=8.7 Hz), 12.1 (brs, 1H). LC-MS: m/z 340 (M+H$^+$);

EXAMPLE 2

2-(2-hydroxy-4-(2-(2-(2-methoxyethoxy)ethoxy)ethoxy)phenyl)-4-methyl-4,5-dihydrooxazole-4-carboxylic acid

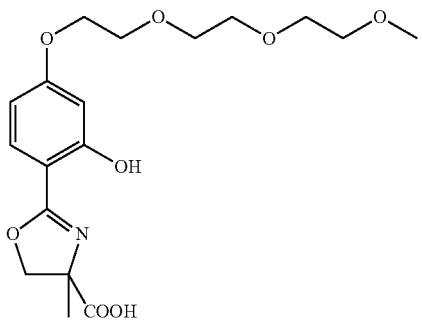 [SMILES: COCCOCCOCCOc1ccc(C2=NC(C)(C(=O)O)CO2)c(O)c1]

Example 2 was prepared as described in Example 1 using 7-(2-(2-(2-methoxyethoxy)ethoxy)ethoxy)-2,2-dimethyl-4H-benzo[d][1,3]dioxin-4-one as a starting material. $^1$H-NMR (300 MHz, DMSO-$d_6$, n=3): δ 1.26 (s, 3H), 3.27 (s, 3H), 3.48-3.60 (m, 8H), 3.74-3.75 (m, 2H), 4.14-4.15 (m, 2H), 4.24 (q, 1H, J=8.7 Hz), 4.75 (q, 1H, J=8.7 Hz), 6.55 (q, 1H, J=8.7 Hz), 6.57 (s, 1H), 7.53-7.56 (q, 1H, J=8.7 Hz), 12.1 (brs, 1H). LC-MS: m/z 384 (M+H$^+$).

EXAMPLE 3

2-(2-hydroxy-4-(2-(2-methoxyethoxy)ethoxy)phenyl)-4-methyl-4,5-dihydro-1H-imidazole-4-carboxylic acid

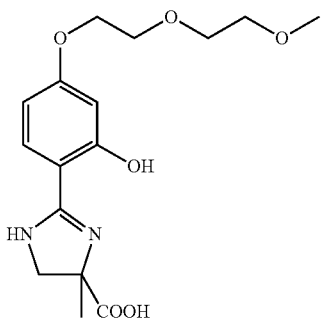 [SMILES: COCCOCCOc1ccc(C2=NC(C)(C(=O)O)CN2)c(O)c1]

Step 1

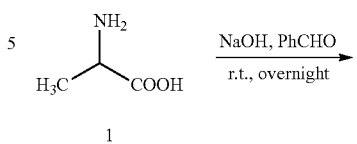

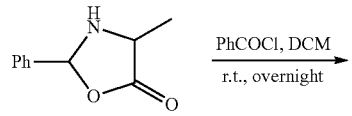

3-benzoyl-4-methyl-2-phenyloxazolidin-5-one (DL)-Alanine (32.9 g, 370 mmol) was added to a solution of NaOH (15.1 g, 370 mmol) in H$_2$O (50 mL) followed by methanol (250 mL). The mixture was heated until the solid dissolved. The solvent was then evaporated until precipitation formed (~30 mL residue). The residue was dissolved in ethanol (250 mL) and benzaldehyde (59 g, 556 mmol) was added. This mixture was stirred at room temperature for 3 h. Ethanol and most of water was removed under vacuum. The residue was dissolved in ethanol (200 mL) and dried over 4 Å molecular sieves. Filtration and evaporation of the solvent gave a white solid which was dried under vacuum overnight. This solid was suspended in dichloromethane (500 mL), and a solution of benzoyl chloride (52.0 g, 370 mmol) in dichloromethane (100 mL) was added dropwise at 0° C. After 3 h at 0° C., the reaction mixture was allowed to stir at room temperature overnight. This suspension/mixture was washed with H$_2$O, 5% NaHCO$_3$, 5% of NaHSO$_3$, and H$_2$O sequentially, then dried over Na$_2$SO$_4$. Evaporation of the solvent gave a white solid. Fractional recrystallizations of this solid from CH$_2$Cl$_2$ and ether (1:2) gave white crystals of 3-benzoyl-4-methyl-2-phenyloxazolidin-5-one (60 g, 58%). LC-MS (ES, m/z): 282 [M+H]$^+$.

Step 2

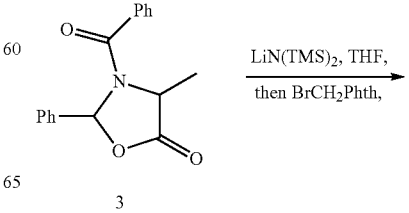

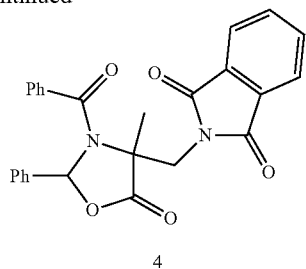

4

2-((3-benzoyl-4-methyl-5-oxo-2-phenyloxazolidin-4-yl)methyl)isoindoline-1,3-dione Into a solution of hexamethyldisilazane (17.5 g, 106 mmol) in THF (100 mL) was added n-butyllithium (1.58 M in hexane, 50 mL, 78.5 mmol) at −78° C. After 5 min at −78° C., the solution was allowed to warm to 0° C. for 30 min and then cooled to −78° C. again. A solution of 3-benzoyl-4-methyl-2-phenyl-1,3-oxazolidin-5-one (dried overnight in vacuo before using, 20 g, 71 mmol) in THF (250 mL) was added slowly under argon, and the dark red brown solution was stirred at this temperature for 3 h. A solution of N-(bromomethyl)phthalimide (22.2 g, 92.5 mmol) in THF (200 mL) was then added dropwise. The reaction mixture was allowed to warm to 20° C. in 4 h and stirred at this temperature overnight. The solvent was evaporated. The residue was dissolved in 10% NH$_4$Cl (250 mL) and extracted with CH$_2$Cl$_2$. The organic phase was dried over Na$_2$SO$_4$ and evaporated. Recrystallization from CH$_2$Cl$_2$ and ether (1:4) gave white crystals of 2-((3-benzoyl-4-methyl-5-oxo-2-phenyloxazolidin-4-yl)methyl)isoindoline-1,3-dione (23 g, 74%). LC-MS (ES, m/z): 441 [M+H]$^+$.

Step 3

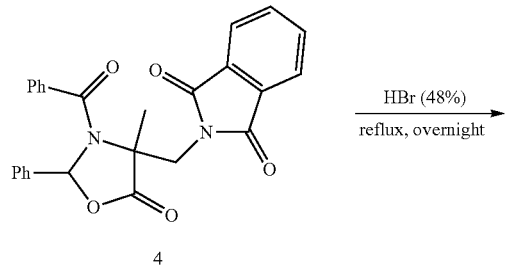

2,3-diamino-2-methylpropanoic acid dihydrobromide

A solution of 2((3-benzoyl-4-methyl-5-oxo-2-phenyloxazolidin-4-yl)methyl)isoindoline-1,3-dione (21 g, 0.5 mol) in 48% of HBr (200 mL) was heated at reflux (120° C. oil bath) overnight. After being extracted with dichloromethane, the aqueous layer was evaporated to give a brownish white crystalline material (14.5 g) of crude diamino acid dihydrobromide salt. LC-MS (ES, m/z): 119 [M+H]$^+$.

Step 4

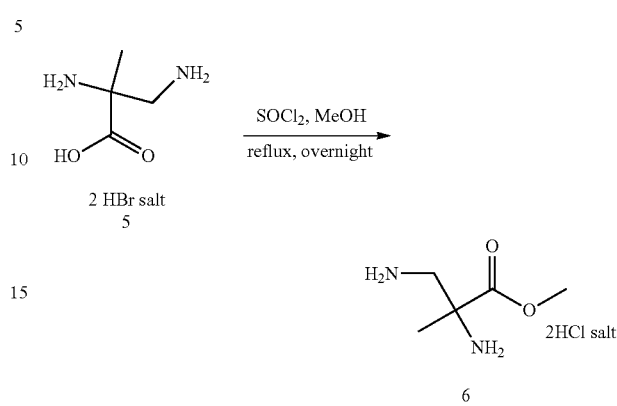

methyl 2,3-diamino-2-methylpropanoate dihydrochloride

Thionyl chloride (60 g, 0.50 mmol) was added to methanol (130 mL) at −10° C. slowly, and then the solution was stirred at room temperature for 30 min. Diamino acid dihydrobromide salt (14.5 g) was added, and the solution was heated at reflux overnight. Evaporation of the solvent followed by drying under vacuum gave a yellowish foam (14.5 g, crude) which used without further purification. LC-MS (ES, m/z): 133 [M+H]$^+$.

Step 5

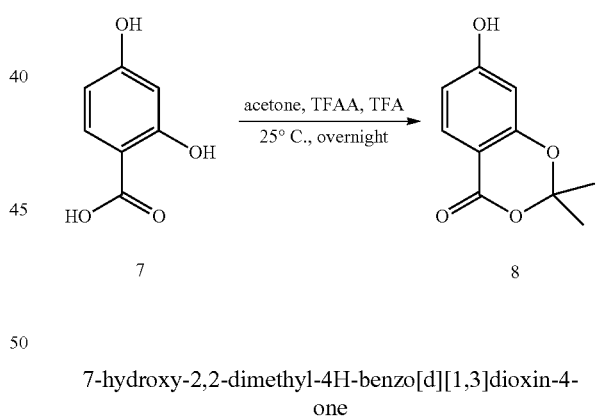

7-hydroxy-2,2-dimethyl-4H-benzo[d][1,3]dioxin-4-one

A suspension of 2,4-dihydroxybenzoic acid (85.0 g) in trifluoroacetic acid (800 mL) was cooled in an ice/water bath. Trifluoroacetic anhydride (500 mL) was added followed by acetone (100 mL). After the addition was complete, the ice/water bath was removed and the reaction mixture stirred for 24 hours before the volatiles were removed under vacuum using a rotary evaporator. The residue was cautiously added to a water/sodium bicarbonate suspension to afford a neutralized mixture. The mixture was extracted with ethyl acetate and the combined organic phases were washed with brine, dried over magnesium sulfate, filtered and evaporated. The residue was triturated with dichloromethane to afford the product as an off-white solid (50 g).

Step 6

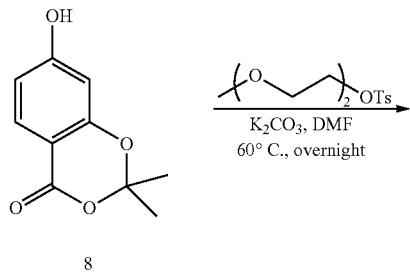

8

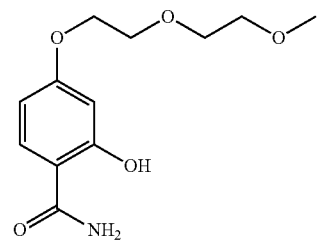

2-hydroxy-4-(2-(2-methoxyethoxy)ethoxy)benzamide 7-(2-(2-methoxyethoxy)ethoxy)-2,2-dimethyl-4H-benzo[d][1,3]dioxin-4-one 2,4-dihy-droxybenzoic acid (22 g) was dissolved in i-PrOH (100 mL). Ammonia gas was bubbled into the solution for 0.5 h at −15° C. The resulting solution was heated to 80° C. overnight in a sealed tube. The reaction was monitored by LCMS. The solution was evaporated under vacuum and purified by silicon column (EtOAc/PE=1/1) to obtain the title compound (15 g). LC-MS (ES, m/z): 256 [M+H]$^+$.

Step 8

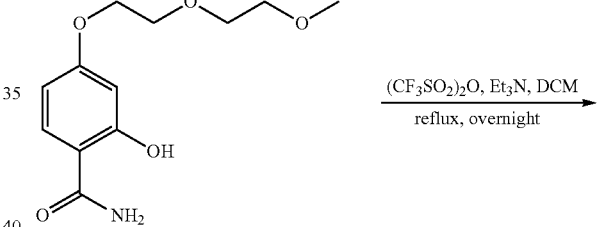

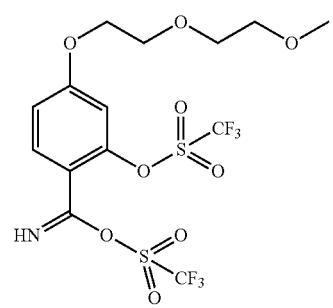

11

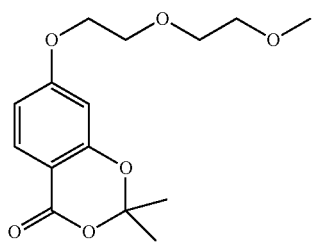

9

7-(2-(2-methoxyethoxy)ethoxy)-2,2-dimethyl-4H-benzo[d][1,3]dioxin-4-one

A solution of 7-hydroxy-2,2-dimethyl-4H-benzo[d][1,3]dioxin-4-one, (19.4 g, 100 mmol), 2-(2-methoxyethoxy)ethyl 4-methylbenzenesulfonate (27.4 g, 100 mmol) and K$_2$CO$_3$ (41 g, 300 mmol) in CH$_3$CN (500 mL) was refluxed for 4.5 hours. The mixture was poured in H$_2$O (1000 mL) and extracted twice with CH$_2$Cl$_2$ (500 mL). The combined organic layers were washed with brine (100 mL), dried over MgSO$_4$, filtered and concentrated under reduced pressure. The crude product was purified by flash chromatography (PE/EtOAc=9/1) to give the title compound (22 g) as white solid. LC-MS (ES, m/z): 297 [M+H]$^+$.

Step 7

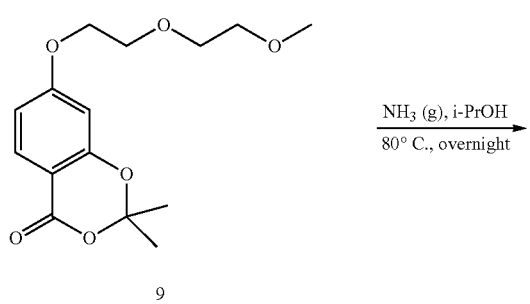

9

Compound 11:

To a solution of 2-hydroxy-4-(2-(2-methoxyethoxy)ethoxy)benzamide (15.0 g) in DCM (200 mL) was added Et$_3$N (17 g, 3eq.). (CF$_3$SO$_2$)$_2$O (50 g, 3eq.) was added dropwise into the mixture at 0° C., and the resulting solution was heated to reflux overnight. The solvent was evaporated under vacuum and the residue was purified by silicon column (EtOAc/PE=1/10) to obtain the title compound as brown oil (20 g).

Step 9

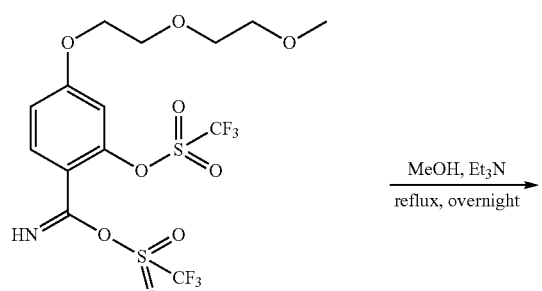

11

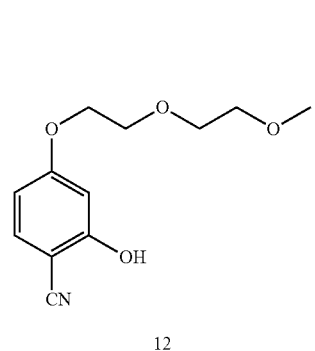

2-hydroxy-4-(2-(2-methoxyethoxy)ethoxy)benzonitrile

To a solution of compound 11 (20 g) in MeOH (300 mL) was added Et$_3$N (20 mL) and the resulting solution was refluxed overnight. The solvent was evaporated under vacuum and the residue was purified by silicon column (EtOAc/PE=1/5) to obtain the title compound as yellow solid (6 g). LC-MS (ES, m/z): 238 [M+H]$^+$.

Step 10

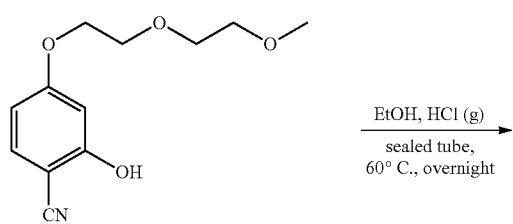

12 ethyl 2-hydroxy-4-(2-(2-methoxyethoxy)ethoxy)benzimidate hydrochloride

A solution of 2-hydroxy-4-(2-(2-methoxyethoxy)ethoxy)benzonitrile (6 g) in MeOH/HCl (g) (150 mL) was heated to 60° C. overnight in a sealed tube. The solvent was evaporated under vacuum and the residue (7 g, crude) was used for the next without further purification. LC-MS (ES, m/z): 284 [M+H]$^+$.

Step 11

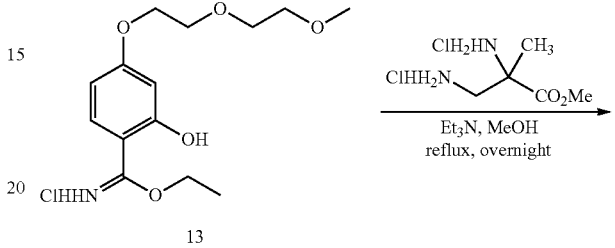

13

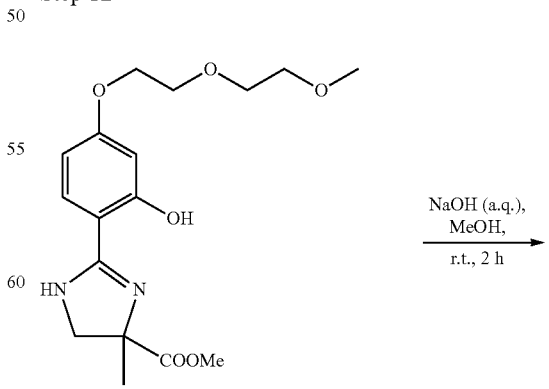

14 methyl 2-(2-hydroxy-4-(2-(2-methoxyethoxy)ethoxy)phenyl)-4-methyl-4,5-dihydro-1H-imidazole-4-carboxylate To a solution of ethyl 2-hydroxy-4-(2-(2-methoxyethoxy)ethoxy)benzimidate hydrochloride (0.35 g, crude, ~1.0 mmol) in MeOH (10 mL) was added methyl 3-amino-2-(chloroamino)-2-methylpropanoate hydrochloride (0.24 g, crude, ~1.0 mmol) followed by dropwise addition of Et$_3$N (1 mL) at 0° C. The resulting solution was refluxed overnight. The solvent was evaporated under vacuum and the residue was purified by prep-HPLC to obtain the title compound as colorless oil (175 mg, 50%). LC-MS (ES, m/z): 353 [M+H]$^+$.

Step 12

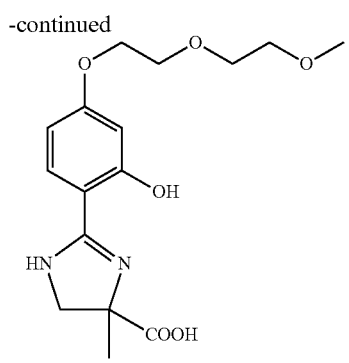

2-(2-hydroxy-4-(2-(2-methoxyethoxy)ethoxy)phenyl)-4-methyl-4,5-dihydro-1H-imidazole-4-carboxylic acid To a solution of methyl 2-(2-hydroxy-4-(2-(2-methoxyethoxy)ethoxy)phenyl)-4-methyl-4,5-dihydro-1H-imidazole-4-carboxylate (0.17 g, 0.5 mmol) in MeOH (5 mL) was added NaOH (40 mg, 1.0 mmol) and water (one drop). The resulting solution was stirred for 2 h at room temperature. The solvent was evaporated under vacuum and the residue was purified by Combi Flash to obtain the title compound as colorless oil (100 mg, 60%). $^1$H NMR (300 MHz, CD$_3$OD, n=2): δ 7.65-7.85 (m, 1H), 6.55-6.75 (m, 2H), 4.30-4.40 (m, 1H), 4.10-4.30 (m, 2H), 3.70-3.95 (m, 2H), 3.65-3.70 (m, 2H), 3.55-3.65 (m, 2H), 3.33 (s, 3H), 1.74 (s, 3H). LC-MS (ES, m/z): 339 [M+H]$^+$.

EXAMPLE 4

2-(2-hydroxy-4-(2-(2-(2-methoxyethoxy)ethoxy)ethoxy)phenyl)-4-methyl-4,5-dihydro-1H-imidazole-4-carboxylic acid

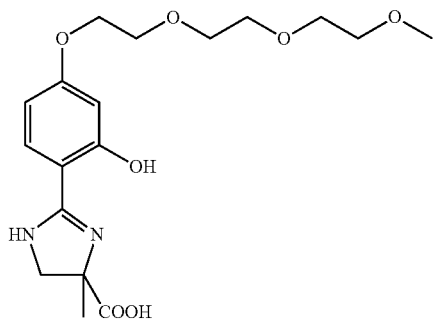 [SMILES: COCCOCCOCCOc1ccc(C2=NC(C)(C(=O)O)CN2)c(O)c1]

Example 4 was prepared as described in Example 3 using 2-(2-(2-methoxyethoxy)ethoxy)ethyl 4-methylbenzenesulfonate as a reagent in Step 6. $^1$H NMR (300 MHz, CD$_3$OD, n=3): δ 7.65-7.85 (m, 1H), 6.55-6.75 (m, 2H), 4.30-4.40 (m, 1H), 4.15-4.25 (m, 2H), 3.75-3.95 (m, 2H), 3.45-3.75 (m, 8H), 3.35 (s, 3H), 1.76 (s, 3H). LC-MS (ES, m/z): 383 [M+H]$^+$.

EXAMPLE 5

2-(2-hydroxy-3-(2-(2-methoxyethoxy)ethoxy)phenyl)-4-methyl-4,5-dihydro-1H-imidazole-4-carboxylic acid

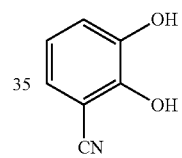

Step 1

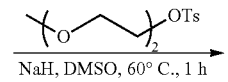

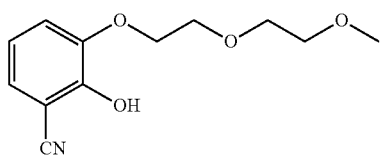

2-hydroxy-3-(2-(2-methoxyethoxy)ethoxy)benzonitrile

To a solution of 2,3-dihydroxybenzonitrile (13.5 g, 1 eq.) in DMSO (200 mL) was added NaH (60%, 8 g, 2eq.) and the resulting solution was stirred for 1 h at 60° C. 2-(2-Methoxyethoxy)ethyl 4-methylbenzenesulfonate (20 g, 0.7eq.) in DMSO (100 mL) was added dropwise at 60° C. and stirring was continued for another 1 h. The reaction was quenched by NH$_4$Cl (sat.), the mixture was extracted with EtOAc (300 mL×3) and the combined organic layers were dried over Na$_2$SO$_4$. The solvent was evaporated and the residue was purified by silicon column (EtOAc/PE=1/1) to give the title compound (6 g, 25%).

LC-MS (ES, m/z): 238 [M+H]$^+$

Step 2

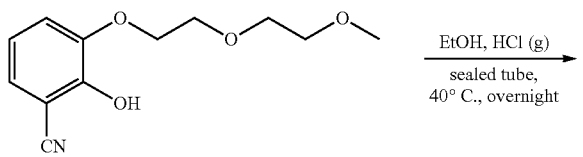

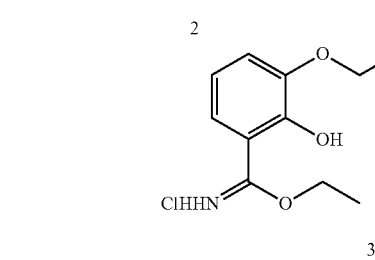

ethyl
2-hydroxy-3-(2-(2-methoxyethoxy)ethoxy)benzimidate
hydrochloride

A solution of 2-hydroxy-3-(2-(2-methoxyethoxy)ethoxy) benzonitrile (6 g) in EtOH/HCl (g) (150 mL) was heated to 40° C. overnight in a sealed tube. The solvent was evaporated under vacuum and the residue (7 g, crude) was used for the next step without further purification.
LC-MS (ES, m/z): 284 [M+H]$^+$ Step 3

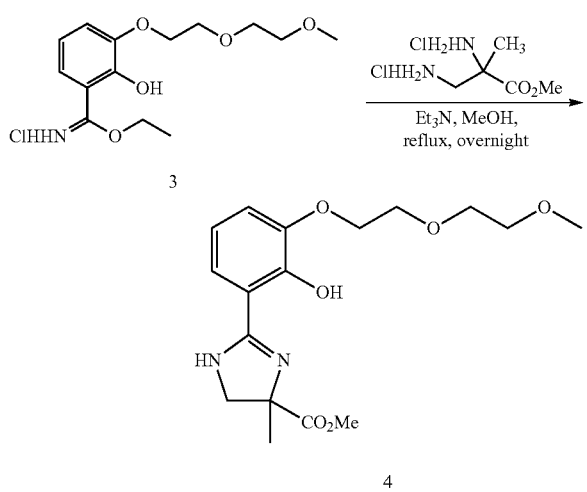

methyl 2-(2-hydroxy-3-(2-(2-methoxyethoxy)
ethoxy)phenyl)-4-methyl-4,5-dihydro-1H-imidazole-
4-carboxylate To a solution of ethyl 2-hydroxy-4-(2-(2-methoxyethoxy) ethoxy)benzimidate hydrochloride (0.35 g, crude, ~1.0 mmol) in MeOH (10 mL) was added methyl 3-amino-2-(chloroamino)-2-methylpropanoate hydrochloride (0.24 g, crude, ~1.0 mmol). Et$_3$N (1 mL) was added dropwise at 0° C. The resulting solution was refluxed overnight. The solvent was evaporated under vacuum and the residue was purified by prep-HPLC to obtain the title compound as colorless oil (90 mg, 25%). LC-MS (ES, m/z): 353 [M+H]$^+$.

Step 4

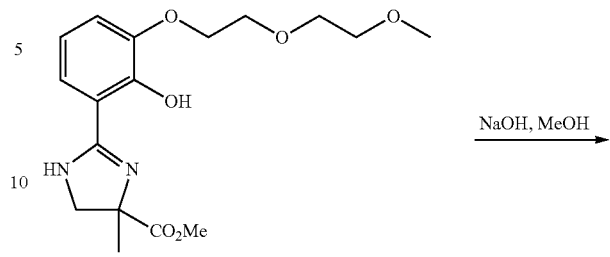

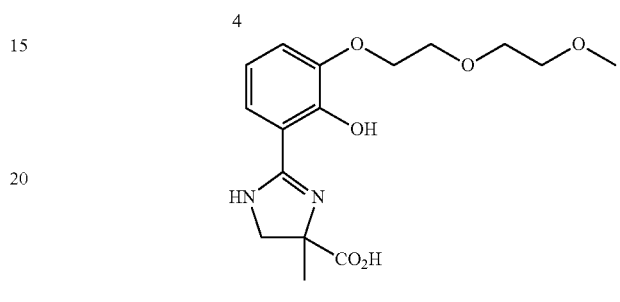

2-(2-hydroxy-3-(2-(2-methoxyethoxy)ethoxy)phe-
nyl)-4-methyl-4,5-dihydro-1H-imidazole-4-carboxy-
lic acid To a solution of methyl 2-(2-hydroxy-3-(2-(2-methoxyethoxy)ethoxy)phenyl)-4-methyl-4,5-dihydro-1H-imidazole-4-carboxylate (0.85 g, 0.25 mmol) in MeOH (5 mL) was added NaOH (20 mg, 0.5 mmol) and water (one drop). The resulting mixture was stirred for 2 h at room temperature. The solvent was evaporated under vacuum and the residue was purified by Combi Flash to obtain the title compound as colorless oil (50 mg, 60%). $^1$H NMR (300 MHz, CD$_3$OD, n=2): δ 7.40-7.50 (m, 1H), 7.10-7.25 (m, 1H), 6.75-6.95 (m, 1H), 4.30-4.40 (m, 1H), 4.15-4.25 (m, 2H), 3.75-3.95 (m, 2H), 3.45-3.75 (m, 5H), 3.35 (s, 3H), 1.67 (s, 3H). LC-MS (ES, m/z): 339 [M+H]$^+$.

EXAMPLE 6

2-(2-hydroxy-3-(2-(2-(2-methoxyethoxy)ethoxy)
ethoxy)phenyl)-4-methyl-4,5-dihydro-1H-imidazole-
4-carboxylic acid

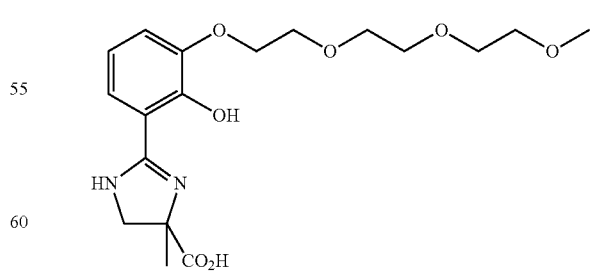

Example 6 was prepared as described in Example 5 using 2-(2-(2-methoxyethoxy)ethoxy)ethyl 4-methylbenzenesulfonate as a reagent in Step 1. $^1$H NMR (300 MHz, CD$_3$OD, n=3): δ 7.30-7.40 (m, 1H), 7.10-7.25 (m, 1H), 6.75-6.95 (m, 1H), 4.30-4.40 (m, 1H), 4.15-4.25 (m, 2H), 3.85-4.00 (m, 2H), 3.45-3.80 (m, 9H), 3.35 (s, 3H), 1.69 (s, 3H). LC-MS (ES, m/z): 383 [M+H]$^+$.

EXAMPLE 7

1-(2-hydroxy-4-(2-(2-methoxyethoxy)ethoxy)phenyl)-1H-pyrazole-3-carboxylic acid

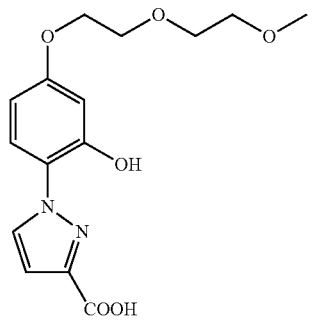 [SMILES: COCCOCCOc1ccc(-n2ccc(C(=O)O)n2)c(O)c1]

Step 1

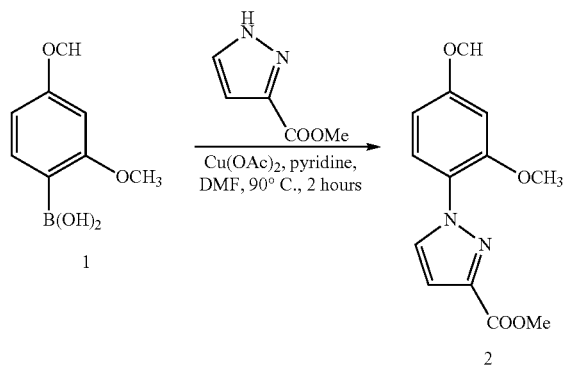

methyl 1(2,4-dimethoxyphenyl)-1H-pyrazole-3-carboxylate (2)

To a solution of 2,4-dimethoxyphenylboronic acid 1 (2.88 g, 15.8 mmol, 1.00 equiv) in DMF (100 mL) was added methyl 1H-pyrazole-3-carboxylate (3.00 g, 23.7 mmol, 1.50 equiv), Cu(OAc)$_2$ (5.70 g, 31.6 mmol, 2.00 equiv), and pyridine (3.76 g, 47.4 mmol, 3 equiv). The resulting solution was stirred for 2 h at 90° C. The solids were filtrated off by filtration and the filtrate was extracted by EtOAc (200 mL×3). The combined organic layers were dried by anhydrous sodium sulfate and concentrated under vacuum. The residue was applied onto a silica gel column and eluted with PE/EA (3/1). This resulted in 1.5 g (36%) of methyl 1-(2,4-dimethoxyphenyl)-1H-pyrazole-3-carboxylate 2 as a brown solid. $^1$H NMR (300 MHz, CDCl$_3$): δ 7.88 (d, J=2.4 Hz, 1H), 7.61 (d, J=9 Hz, 1H), 6.97 (d, J=2.4 Hz, 1H), 6.59 (s, 1H), 7.73, 6.58 (d, J=8.7 Hz, 1H). LC-MS: m/z=263 (MH)$^+$.

Step 2

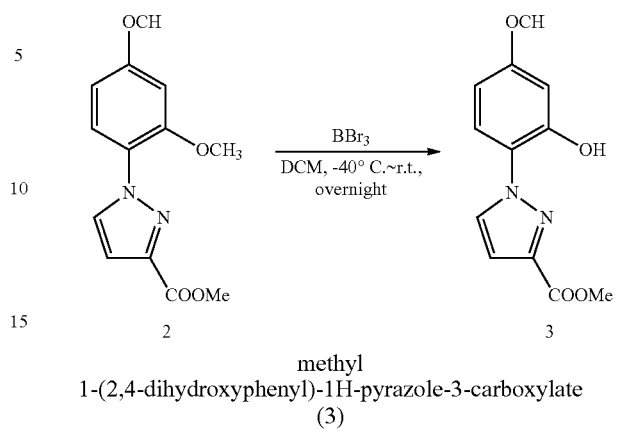

methyl 1-(2,4-dihydroxyphenyl)-1H-pyrazole-3-carboxylate (3)

To a solution of methyl 1-(2,4-dimethoxyphenyl)-1H-pyrazole-3-carboxylate 2 (1.00 g, 3.82 mmol, 1.00 equiv) in DCM (20 mL) was added BBr$_3$ (9.55 g, 38.2 mmol, 10 equiv) at −40° C. The resulting solution was stirred overnight at room temperature. The mixture was quenched by the addition of 10 mL of water and the reaction mixture was extracted with 3×200 mL of ethyl acetate. The combined organic layers were washed with 200 mL of brine, dried over anhydrous sodium sulfate and concentrated under vacuum. This resulted in 0.8 g (90%) of methyl 1-(2,4-dihydroxyphenyl)-1H-pyrazole-3-carboxylate 3 as a white solid. LC-MS: m/z=235 (MH)$^+$.

Step 3

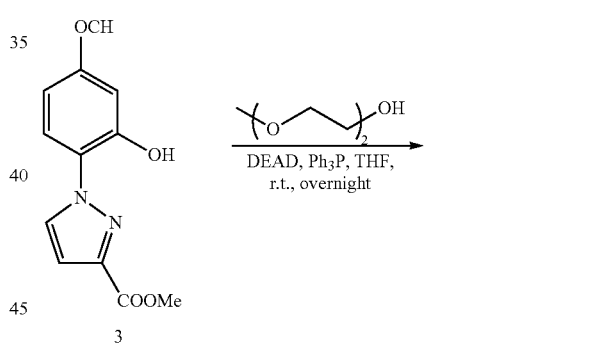

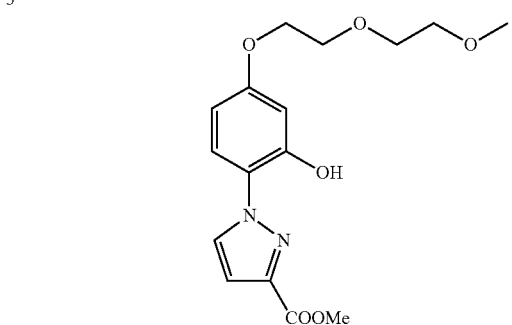

methyl 1-(2-hydroxy-4-(2-(2-methoxyethoxy)ethoxy)phenyl)-1H-pyrazole-3-carboxylate (4)

To a solution of methyl 1-(2,4-dihydroxyphenyl)-1H-pyrazole-3-carboxylate 3 (200 mg, 0.855 mmol, 1.00 equiv) in THF (5 mL), 2-(2-methoxyethoxy)ethanol (103 mg, 0.855 mmol, 1.00 equiv) was added Ph$_3$P (223 mg, 0.855 mmol, 1.00 equiv), and DEAD (149 mg, 0.855 mmol, 1.00 equiv) at 0° C. The resulting solution was stirred overnight. The solvent was concentrated under vacuum, the residue was applied onto a silica gel column and eluted with PE/EA (1/1). This resulted in 70 mg (50%) of methyl 1-(2-hydroxy-4-(2-(2-methoxyethoxy)ethoxy)phenyl)-1H-pyrazole-3-carboxylate 4 as a green oil.

LC-MS: m/z=337 (MH)$^+$.

Step 4

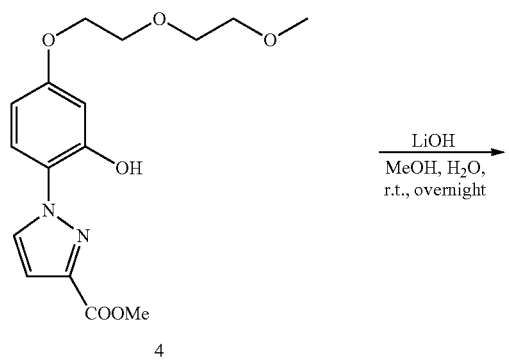

1-(2-hydroxy-4-(2-(2-methoxyethoxy)ethoxy)phenyl)-1H-pyrazole-3-carboxylic acid (5)

To a solution of methyl 1-(2-hydroxy-4-(2-(2-methoxyethoxy)ethoxy)phenyl)-1H-pyrazole-3-carboxylate 4 (70 mg, 0.208 mmol, 1.00 equiv) in methanol (10 mL), LiOH (50%, 6 mg, 0.250 mmol, 1.20 equiv) was added. The resulting solution was stirred overnight at room temperature. The solvent was concentrated under vacuum, the residue was applied onto a silica gel column and eluted with DCM/MeOH (3/1). This resulted in 60 mg (89%) of 1-(2-hydroxy-4-(2-(2-methoxyethoxy)ethoxy)-phenyl)-1H-pyrazole-3-carboxylic acid 5 as a green oil. $^1$H NMR (300 MHz, CDCl$_3$, n=2): δ 8.00-8.10 (m, 1H), 7.35-7.60 (m, 1H), 6.85-7.00 (m, 1H), 6.30-6.70 (m, 2H), 4.10-4.15 (m, 2H), 3.70-3.85 (m, 2H), 3.45-3.70 (m, 4H), 3.43 (s, 3H). LC-MS: m/z=323 (MH)

EXAMPLE 8

1-(2-hydroxy-4-(2-(2-(2-methoxyethoxy)ethoxy)ethoxy)phenyl)-1H-pyrazole-3-carboxylic acid

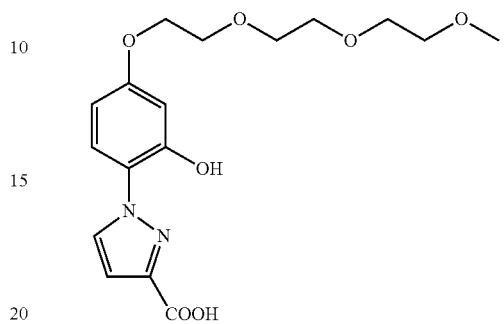

Example 8 was prepared as described in Example 7 using 2-(2-(2-methoxyethoxy)ethoxy)ethanol as a reagent in Step 3. $^1$H NMR (300 MHz, DMSO-d6, n=3): δ 9.93 (br, 1H), 8.14 (m, 1H), 7.41 (m, 1H), 6.82 (m, 1H), 6.50 (m, 1H), 4.16 (m, 2H), 3.75-3.85 (m, 2H), 3.10-3.70 (m, 11H). LC-MS: m/z=367 (MH).

The following compounds can generally be made using the methods known in the art and described above. It is expected that these compounds when made will have activity similar to those that have been made in the examples above.

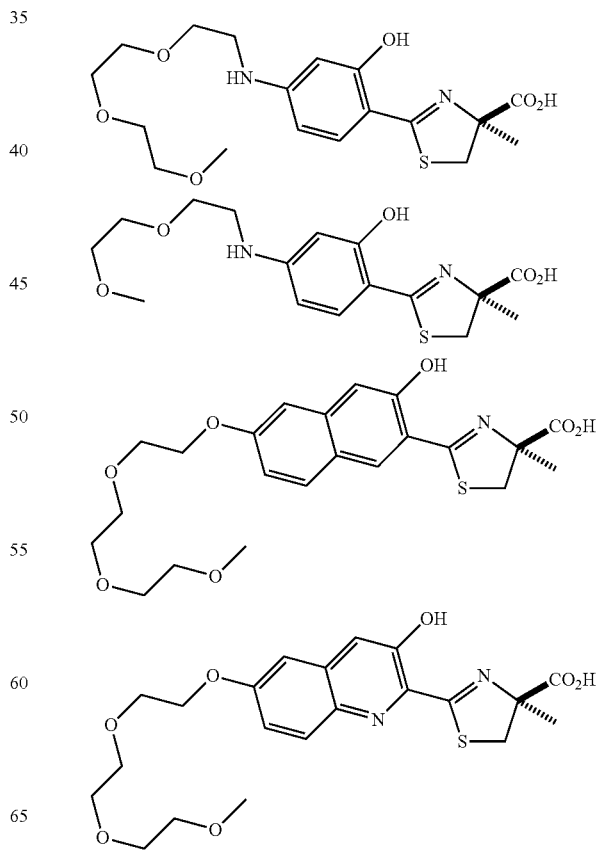

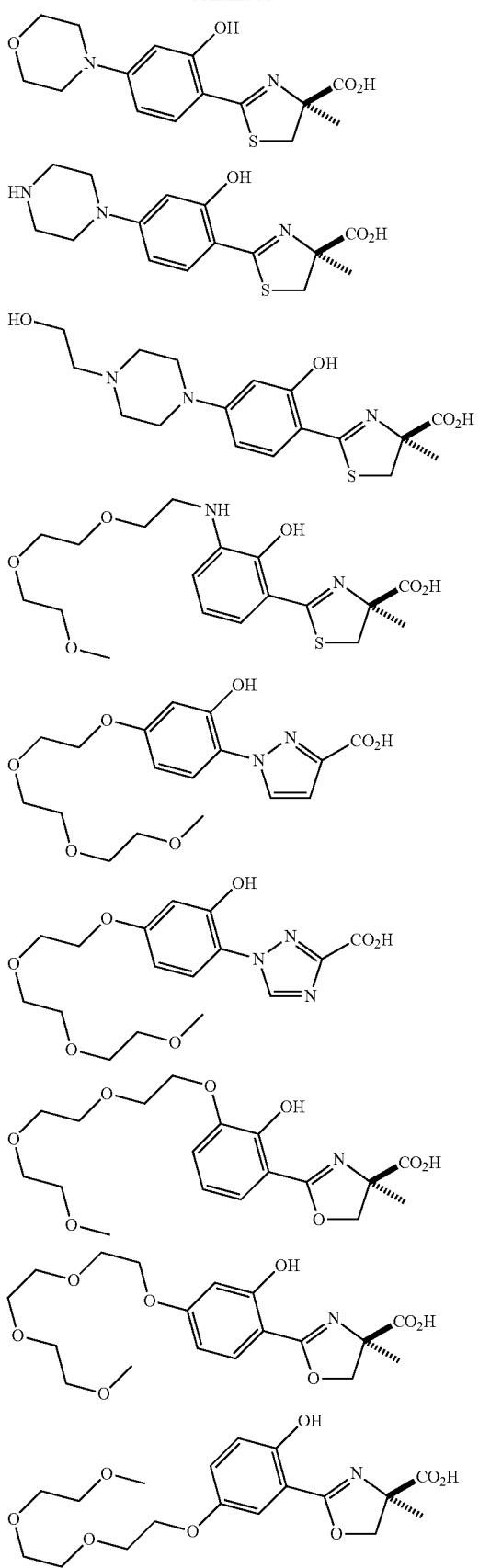

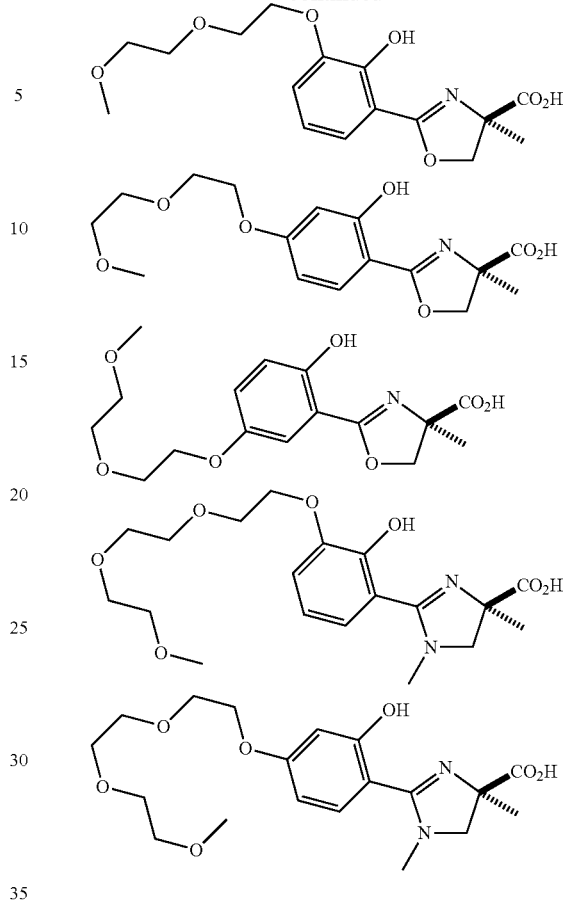

The invention is further illustrated by the following examples. The following compounds may be represented herein using the Simplified Molecular Input Line Entry System, or SMILES. SMILES is a modern chemical notation system, developed by David Weininger and Daylight Chemical Information Systems, Inc., that is built into all major commercial chemical structure drawing software packages. Software is not needed to interpret SMILES text strings, and an explanation of how to translate SMILES into structures can be found in Weininger, D., *J. Chem. Inf. Comput. Sci.* 1988, 28, 31-36. All SMILES strings used herein, as well as many IUPAC names, were generated using CambridgeSoft's ChemDraw 11.0.

C[C@]1(C(O)=O)CSC(C2=C(O)C(OCCOCCOCCN(C)C)=CC=C2)=N1

[CO2H][C@@]1(C)CSC(C2=C(O)C(OCCOCCN(C)C)=CC=C2)=N1

C[C@]1(C(O)=O)CSC(C2=C(O)C=C(OCCOCCOCCN(C)C)C=C2)=N1

C[C@]1(C(O)=O)CSC(C2=C(O)C=C(OCCOCCN(C)C)C=C2)=N1

C[C@]1(C(O)=O)CSC(C2=C(O)C=CC(OCCOCCOCCN(C)C)=C2)=N1

C[C@]1(C(O)=O)CSC(C2=C(O)C=CC(OCCOCCN(C)C)=C2)=N1

[CO2Et][C@@]1(C)CSC(C2=C(O)C(OCCOCCOCCN(C)C)=CC=C2)=N1

[CO2Et][C@@]1(C)CSC(C2=C(O)C(OCCOCCN(C)C)=CC=C2)=N1

[CO2Et][C@@]1(C)CSC(C2=C(O)C=C(OCCOCCOCCN(C)C)C=C2)=N1

[CO2Et][C@@]1(C)CSC(C2=C(O)C=C(OCCOCCN(C)C)C=C2)=N1
[CO2Et][C@@]1(C)CSC(C2=C(O)C=CC(OCCOCCOCCN(C)C)=C2)=N1
[CO2Et][C@@]1(C)CSC(C2=C(O)C=CC(OCCOCCN(C)C)=C2)=N1
C[C@]1(C(O)=O)CN(C)C(C2=C(O)C(OCCOCCOCCN(C)C)=CC=C2)=N1
C[C@]1(C(O)=O)CN(C)C(C2=C(O)C(OCCOCCN(C)C)=CC=C2)=N1
C[C@]1(C(O)=O)CN(C)C(C2=C(O)C=C(OCCOCCOCCN(C)C)C=C2)=N1
C[C@]1(C(O)=O)CN(C)C(C2=C(O)C=C(OCCOCCN(C)C)C=C2)=N1
C[C@]1(C(O)=O)CN(C)C(C2=C(O)C=CC(OCCOCCOCCN(C)C)=C2)=N1
C[C@]1(C(O)=O)CN(C)C(C2=C(O)C=CC(OCCOCCN(C)C)=C2)=N1
[CO2Et][C@@]1(C)CN(C)C(C2=C(O)C(OCCOCCOCCN(C)C)=CC=C2)=N1
[CO2Et][C@@]1(C)CN(C)C(C2=C(O)C(OCCOCCN(C)C)=CC=C2)=N1
[CO2Et][C@@]1(C)CN(C)C(C2=C(O)C=C(OCCOCCOCCN(C)C)C=C2)=N1
[CO2Et][C@@]1(C)CN(C)C(C2=C(O)C=C(OCCOCCN(C)C)C=C2)=N1
[CO2Et][C@@]1(C)CN(C)C(C2=C(O)C=CC(OCCOCCOCCN(C)C)=C2)=N1
[CO2Et][C@@]1(C)CN(C)C(C2=C(O)C=CC(OCCOCCN(C)C)=C2)=N1
C[C@]1(C(O)=O)COC(C2=C(O)C(OCCOCCOCCN(C)C)=CC=C2)=N1
C[C@]1(C(O)=O)COC(C2=C(O)C(OCCOCCN(C)C)=CC=C2)=N1
C[C@]1(C(O)=O)COC(C2=C(O)C=C(OCCOCCOCCN(C)C)C=C2)=N1
C[C@]1(C(O)=O)COC(C2=C(O)C=C(OCCOCCN(C)C)C=C2)=N1
C[C@]1(C(O)=O)COC(C2=C(O)C=CC(OCCOCCOCCN(C)C)=C2)=N1
C[C@]1(C(O)=O)COC(C2=C(O)C=CC(OCCOCCN(C)C)=C2)=N1
[CO2Et][C@@]1(C)COC(C2=C(O)C(OCCOCCOCCN(C)C)=CC=C2)=N1
[CO2Et][C@@]1(C)COC(C2=C(O)C(OCCOCCN(C)C)=CC=C2)=N1
[CO2Et][C@@]1(C)COC(C2=C(O)C=C(OCCOCCOCCN(C)C)C=C2)=N1
[CO2Et][C@@]1(C)COC(C2=C(O)C=C(OCCOCCN(C)C)C=C2)=N1
[CO2Et][C@@]1(C)COC(C2=C(O)C=CC(OCCOCCOCCN(C)C)=C2)=N1
[CO2Et][C@@]1(C)COC(C2=C(O)C=CC(OCCOCCN(C)C)=C2)=N1
C[C@]1(C(O)=O)CN(C)C(C2=C(O)C(N3CCOCC3)=CC=C2)=N1
C[C@]1(C(O)=O)CN(C)C(C2=C(O)C=C(N3CCOCC3)C=C2)=N1
C[C@]1(C(O)=O)CN(C)C(C2=C(O)C=CC(N3CCOCC3)=C2)=N1
C[C@]1(C(O)=O)CN(C)C(C2=C(O)C(N3CCNCC3)=CC=C2)=N1
C[C@]1(C(O)=O)CN(C)C(C2=C(O)C=C(N3CCNCC3)C=C2)=N1
C[C@]1(C(O)=O)CN(C)C(C2=C(O)C=CC(N3CCNCC3)=C2)=N1
C[C@]1(C(O)=O)CN(C)C(C2=C(O)C(N3CCN(CCO)CC3)=CC=C2)=N1
C[C@]1(C(O)=O)CN(C)C(C2=C(O)C=C(N3CCN(CCO)CC3)C=C2)=N1
C[C@]1(C(O)=O)CN(C)C(C2=C(O)C=CC(N3CCN(CCO)CC3)=C2)=N1
C[C@]1(C(O)=O)CN(C)C(C2=C(O)C=CC(N3CCN(CCOC)CC3)=C2)=N1
C[C@]1(C(O)=O)COC(C2=C(O)C(N3CCOCC3)=CC=C2)=N1
C[C@]1(C(O)=O)COC(C2=C(O)C=C(N3CCOCC3)C=C2)=N1
C[C@]1(C(O)=O)COC(C2=C(O)C=CC(N3CCOCC3)=C2)=N1
C[C@]1(C(O)=O)COC(C2=C(O)C=C(N3CCNCC3)C=C2)=N1
C[C@]1(C(O)=O)COC(C2=C(O)C=C(N3CCNCC3)C=C2)=N1
C[C@]1(C(O)=O)COC(C2=C(O)C=CC(N3CCNCC3)=C2)=N1
C[C@]1(C(O)=O)COC(C2=C(O)C=C(N3CCN(CCO)CC3)C=C2)=N1
C[C@]1(C(O)=O)COC(C2=C(O)C=CC(N3CCN(CCO)CC3)=C2)=N1
C[C@]1(C(O)=O)COC(C2=C(O)C=CC(N3CCN(CCOC)CC3)=C2)=N1
C[C@]1(C(O)=O)CSC(C2=C(O)C(N3CCOCC3)=CC=C2)=N1
C[C@]1(C(O)=O)CSC(C2=C(O)C=C(N3CCOCC3)C=C2)=N1
C[C@]1(C(O)=O)CSC(C2=C(O)C=CC(N3CCOCC3)=C2)=N1
C[C@]1(C(O)=O)CSC(C2=C(O)C=C(N3CCNCC3)C=C2)=N1
C[C@]1(C(O)=O)CSC(C2=C(O)C=C(N3CCNCC3)C=C2)=N1
C[C@]1(C(O)=O)CSC(C2=C(O)C=CC(N3CCNCC3)=C2)=N1
C[C@]1(C(O)=O)CSC(C2=C(O)C(N3CCN(CCO)CC3)=CC=C2)=N1
C[C@]1(C(O)=O)CSC(C2=C(O)C=C(N3CCN(CCO)CC3)C=C2)=N1
C[C@]1(C(O)=O)CSC(C2=C(O)C=CC(N3CCN(CCO)CC3)=C2)=N1
C[C@]1(C(O)=O)CSC(C2=C(O)C=CC(N3CCN(CCOC)CC3)=C2)=N1
C[C@]1(C(O)=O)CN(C)C(C2=C(O)C(N3CCN(CCOC)CC3)=CC=C2)=N1
C[C@]1(C(O)=O)CN(C)C(C2=C(O)C=C(N3CCN(CCOC)CC3)C=C2)=N1
C[C@]1(C(O)=O)CN(C)C(C2=C(O)C(N3CCN(CCN)CC3)=CC=C2)=N1
C[C@]1(C(O)=O)CN(C)C(C2=C(O)C=C(N3CCN(CCN)CC3)C=C2)=N1
C[C@]1(C(O)=O)CN(C)C(C2=C(O)C=CC(N3CCN(CCN)CC3)=C2)=N1
C[C@]1(C(O)=O)COC(C2=C(O)C(N3CCN(CCOC)CC3)=CC=C2)=N1
C[C@]1(C(O)=O)COC(C2=C(O)C=C(N3CCN(CCOC)CC3)C=C2)=N1
C[C@]1(C(O)=O)COC(C2=C(O)C(N3CCN(CCN)CC3)=CC=C2)=N1
C[C@]1(C(O)=O)COC(C2=C(O)C=C(N3CCN(CCN)CC3)C=C2)=N1
C[C@]1(C(O)=O)COC(C2=C(O)C=CC(N3CCN(CCN)CC3)=C2)=N1

C[C@]1(C(O)=O)CSC(C2=C(O)C(N3CCN(CCOC)CC3)=CC=C2)=N1
C[C@]1(C(O)=O)CSC(C2=C(O)C=C(N3CCN(CCOC)CC3)C=C2)=N1
C[C@]1(C(O)=O)CSC(C2=C(O)C(N3CCN(CCN)CC3)=CC=C2)=N1
C[C@]1(C(O)=O)CSC(C2=C(O)C=C(N3CCN(CCN)CC3)C=C2)=N1
C[C@]1(C(O)=O)CSC(C2=C(O)C=CC(N3CCN(CCN)CC3)=C2)=N1
C[C@]1(C(O)=O)CN(C)C(C2=C(O)C(NCCOCCOCCN(C)C)=CC=C2)=N1
C[C@]1(C(O)=O)CN(C)C(C2=C(O)C(NCCOCCN(C)C)=CC=C2)=N1
C[C@]1(C(O)=O)CN(C)C(C2=C(O)C=C(NCCOCCOCCN(C)C)C=C2)=N1
C[C@]1(C(O)=O)CN(C)C(C2=C(O)C=C(NCCOCCN(C)C)C=C2)=N1
C[C@]1(C(O)=O)CN(C)C(C2=C(O)C=CC(NCCOCCOCCN(C)C)=C2)=N1
C[C@]1(C(O)=O)CN(C)C(C2=C(O)C=CC(NCCOCCN(C)C)=C2)=N1
[CO2Et][C@@]1(C)CN(C)C(C2=C(O)C(NCCOCCOCCN(C)C)=CC=C2)=N1
[CO2Et][C@@]1(C)CN(C)C(C2=C(O)C(NCCOCCN(C)C)=CC=C2)=N1
[CO2Et][C@@]1(C)CN(C)C(C2=C(O)C=C(NCCOCCOCCN(C)C)C=C2)=N1
[CO2Et][C@@]1(C)CN(C)C(C2=C(O)C=C(NCCOCCN(C)C)C=C2)=N1
[CO2Et][C@@]1(C)CN(C)C(C2=C(O)C=CC(NCCOCCOCCN(C)C)=C2)=N1
[CO2Et][C@@]1(C)CN(C)C(C2=C(O)C=CC(NC-COCCN(C)C)=C2)=N1
C[C@]1(C(O)=O)COC(C2=C(O)C(NCCOCCOCCN(C)C)=CC=C2)=N1
C[C@]1(C(O)=O)COC(C2=C(O)C(NCCOCCN(C)C)=CC=C2)=N1
C[C@]1(C(O)=O)COC(C2=C(O)C=C(NCCOCCOCCN(C)C)C=C2)=N1
C[C@]1(C(O)=O)COC(C2=C(O)C=C(NCCOCCN(C)C)C=C2)=N1
C[C@]1(C(O)=O)COC(C2=C(O)C=CC(NCCOCCOCCN(C)C)=C2)=N1
C[C@]1(C(O)=O)COC(C2=C(O)C=CC(NCCOCCN(C)C)=C2)=N1
[CO2Et][C@@]1(C)COC(C2=C(O)C(NCCOCCOCCN(C)C)=CC=C2)=N1
[CO2Et][C@@]1(C)COC(C2=C(O)C(NCCOCCN(C)C)=CC=C2)=N1
[CO2Et][C@@]1(C)COC(C2=C(O)C=C(NCCOCCOCCN(C)C)C=C2)=N1
[CO2Et][C@@]1(C)COC(C2=C(O)C=C(NCCOCCN(C)C)C=C2)=N1
[CO2Et][C@@]1(C)COC(C2=C(O)C=CC(NCCOCCOCCN(C)C)=C2)=N1
[CO2Et][C@@]1(C)COC(C2=C(O)C=CC(NCCOCCN(C)C)=C2)=N1
C[C@]1(C(O)=O)CSC(C2=C(O)C(NCCOCCOCCN(C)C)=CC=C2)=N1
C[C@]1(C(O)=O)CSC(C2=C(O)C(NCCOCCN(C)C)=CC=C2)=N1
C[C@]1(C(O)=O)CSC(C2=C(O)C=C(NCCOCCOCCN(C)C)C=C2)=N1
C[C@]1(C(O)=O)CSC(C2=C(O)C=C(NCCOCCN(C)C)C=C2)=N1
C[C@]1(C(O)=O)CSC(C2=C(O)C=CC(NCCOCCOCCN(C)C)=C2)=N1
C[C@]1(C(O)=O)CSC(C2=C(O)C=CC(NCCOCCN(C)C)=C2)=N1
[CO2Et][C@@]1(C)CSC(C2=C(O)C(NCCOCCOCCN(C)C)=CC=C2)=N1
[CO2Et][C@@]1(C)CSC(C2=C(O)C(NCCOCCN(C)C)=CC=C2)=N1
[CO2Et][C@@]1(C)CSC(C2=C(O)C=C(NCCOCCOCCN(C)C)C=C2)=N1
[CO2Et][C@@]1(C)CSC(C2=C(O)C=C(NCCOCCN(C)C)C=C2)=N1
[CO2Et][C@@]1(C)CSC(C2=C(O)C=CC(NCCOCCOCCN(C)C)=C2)=N1
[CO2Et][C@@]1(C)CSC(C2=C(O)C=CC(NCCOCCN(C)C)=C2)=N1
C[C@]1(C(O)=O)CN(C)C(C2=C(O)C(NCCOCCOCCOC)=CC=C2)=N1
C[C@]1(C(O)=O)CN(C)C(C2=C(O)C(NCCOCCOC)=CC=C2)=N1
C[C@]1(C(O)=O)CN(C)C(C2=C(O)C=C(NCCOCCOCCOC)C=C2)=N1
C[C@]1(C(O)=O)CN(C)C(C2=C(O)C=C(NCCOCCOC)C=C2)=N1
C[C@]1(C(O)=O)CN(C)C(C2=C(O)C=CC(NCCOCCOCCOC)=C2)=N1
C[C@]1(C(O)=O)CN(C)C(C2=C(O)C=CC(NCCOCCOC)=C2)=N1
[CO2Et][C@@]1(C)CN(C)C(C2=C(O)C(NCCOCCOCCOC)=CC=C2)=N1
[CO2Et][C@@]1(C)CN(C)C(C2=C(O)C(NCCOCCOC)=CC=C2)=N1
[CO2Et][C@@]1(C)CN(C)C(C2=C(O)C=C(NCCOCCOCCOC)C=C2)=N1
[CO2Et][C@@]1(C)CN(C)C(C2=C(O)C=C(NCCOCCOC)C=C2)=N1
[CO2Et][C@@]1(C)CN(C)C(C2=C(O)C=CC(NCCOCCOCCOC)=C2)=N1
[CO2Et][C@@]1(C)CN(C)C(C2=C(O)C=CC(NCCOCCOC)=C2)=N1
C[C@]1(C(O)=O)COC(C2=C(O)C(NCCOCCOCCOC)=CC=C2)=N1
C[C@]1(C(O)=O)COC(C2=C(O)C(NCCOCCOC)=CC=C2)=N1
C[C@]1(C(O)=O)COC(C2=C(O)C=C(NCCOCCOCCOC)C=C2)=N1
C[C@]1(C(O)=O)COC(C2=C(O)C=C(NCCOCCOC)C=C2)=N1
C[C@]1(C(O)=O)COC(C2=C(O)C=CC(NCCOCCOCCOC)=C2)=N1
C[C@]1(C(O)=O)COC(C2=C(O)C=CC(NCCOCCOC)=C2)=N1
[CO2Et][C@@]1(C)COC(C2=C(O)C(NCCOCCOCCOC)=CC=C2)=N1
[CO2Et][C@@]1(C)COC(C2=C(O)C(NCCOCCOC)=CC=C2)=N1
[CO2Et][C@@]1(C)COC(C2=C(O)C=C(NCCOCCOCCOC)C=C2)=N1
[CO2Et][C@@]1(C)COC(C2=C(O)C=C(NCCOCCOC)C=C2)=N1
[CO2Et][C@@]1(C)COC(C2=C(O)C=CC(NCCOCCOCCOC)=C2)=N1
[CO2Et][C@@]1(C)COC(C2=C(O)C=CC(NCCOCCOC)=C2)=N1
C[C@]1(C(O)=O)CSC(C2=C(O)C(NCCOCCOCCOC)=CC=C2)=N1

C[C@]1(C(O)=O)CSC(C2=C(O)C(NCCOCCOC)=CC=C2)=N1
C[C@]1(C(O)=O)CSC(C2=C(O)C=C(NCCOCCOC-COC)C=C2)=N1
C[C@]1(C(O)=O)CSC(C2=C(O)C=C(NCCOCCOC)C=C2)=N1
C[C@]1(C(O)=O)CSC(C2=C(O)C=CC(NCCOCCOC-COC)=C2)=N1
C[C@]1(C(O)=O)CSC(C2=C(O)C=CC(NCCOC-COC)=C2)=N1
[CO2Et][C@@]1(C)CSC(C2=C(O)C(NCCOCCOC-COC)=CC=C2)=N1
[CO2Et][C@@]1(C)CSC(C2=C(O)C(NCCOCCOC-COC)=CC=C2)=N1
[CO2Et][C@@]1(C)CSC(C2=C(O)C=C(NCCOCCOC-COC)C=C2)=N1
[CO2Et][C@@]1(C)CSC(C2=C(O)C=C(NCCOCCOC)C=C2)=N1
[CO2Et][C@@]1(C)CSC(C2=C(O)C=CC(NCCOCCOC-COC)=C2)=N1
[CO2Et][C@@]1(C)CSC(C2=C(O)C=CC(NCCOC-COC)=C2)=N1
C[C@]1(C(O)=O)CN(C)C(C2=C(O)C=CC(OCCOC-COCCOC)=C2)=N1
C[C@]1(C(O)=O)CN(C)C(C2=C(O)C=CC(OCCOC-COC)=C2)=N1
[CO2Et][C@@]1(C)CN(C)C(C2=C(O)C(OCCOCCOC-COC)=CC=C2)=N1
[CO2Et][C@@]1(C)CN(C)C(C2=C(O)C(OCCOCCOC)=CC=C2)=N1
[CO2Et][C@@]1(C)CN(C)C(C2=C(O)C=C(OCCOC-COCCOC)C=C2)=N1
[CO2Et][C@@]1(C)CN(C)C(C2=C(O)C=C(OCCOC-COC)C=C2)=N1
[CO2Et][C@@]1(C)CN(C)C(C2=C(O)C=CC(OCCOC-COCCOC)=C2)=N1
[CO2Et][C@@]1(C)CN(C)C(C2=C(O)C=CC(OCCOC-COC)=C2)=N1
[CO2Et][C@@]1(C)COC(C2=C(O)C(OCCOCCOC-COC)=CC=C2)=N1
[CO2Et][C@@]1(C)COC(C2=C(O)C(OCCOCCOC)=CC=C2)=N1
[CO2Et][C@@]1(C)COC(C2=C(O)C=C(OCCOCCOC-COC)C=C2)=N1
[CO2Et][C@@]1(C)COC(C2=C(O)C=C(OCCOCCOC)C=C2)=N1
[CO2Et][C@@]1(C)COC(C2=C(O)C=CC(OCCOCCOC-COC)=C2)=N1
[CO2Et][C@@]1(C)COC(C2=C(O)C=CC(OCCOC-COC)=C2)=N1
C[C@]1(C(O)=O)CSC(C2=C(O)C(OCCOCCOCCN(C)C)=CC=C2)=N1
C[C@]1(C(O)=O)CSC(C2=C(O)C(OCCOCCN(C)C)=CC=C2)=N1
C[C@]1(C(O)=O)CSC(C2=C(O)C=C(OCCOCCOCCN(C)C)C=C2)=N1
C[C@]1(C(O)=O)CSC(C2=C(O)C=C(OCCOCCN(C)C)C=C2)=N1
C[C@]1(C(O)=O)CSC(C2=C(O)C=CC(OCCOC-COCCN(C)C)=C2)=N1
C[C@]1(C(O)=O)CSC(C2=C(O)C=CC(OCCOCCN(C)C)=C2)=N1
[CO2Et][C@@]1(C)CSC(C2=C(O)C(OCCOCCOCCN(C)C)=CC=C2)=N1
[CO2Et][C@@]1(C)CSC(C2=C(O)C(OCCOCCN(C)C)=CC=C2)=N1

[CO2Et][C@@]1(C)CSC(C2=C(O)C=C(OCCOC-COCCN(C)C)C=C2)=N1
[CO2Et][C@@]1(C)CSC(C2=C(O)C=C(OCCOCCN(C)C)C=C2)=N1
[CO2Et][C@@]1(C)CSC(C2=C(O)C=CC(OCCOC-COCCN(C)C)=C2)=N1
[CO2Et][C@@]1(C)CSC(C2=C(O)C=CC(OCCOCCN(C)C)=C2)=N1
OC(C(OCCOCCOCCOC)=CC=C1)=C1N2N=C(C(O)=O)C=C2
OC(C(OCCOCCOCCOC)=CC=C1)=C1N2N=C(C(O)=O)N=C2
[CO2Et]C1=NN(C2=C(O)C(OCCOCCOCCOC)=CC=C2)C=C1
[CO2Et]C1=NN(C2=C(O)C(OCCOCCOCCOC)=CC=C2)C=N1
C[C@]1(C(O)=O)CSC(C2=C(O)C=C(C=CC(OCCOC-COCCCOC)=C3)C3=C2)=N1
C[C@]1(C(O)=O)CSC(C2=C(O)C=C(C=CC(OCCOC-COCCCOC)=C3)C3=N2)=N1
OC(C=C(C=CC(OCCOCCOCCOC)=C1)C1=C2)=C2C3=NC(C(O)=O)CS 3
OC(C=C(C=CC(OCCOCCOCCOC)=C1)C1=N2)=C2C3=NC(C(O)=O)CS 3
O=C(OC(C)C)C1=NN(C=N1)C2=CC=C(OC-CCNCCCNCCCN(C)C)=C2O
O=C(OCC)C1=NN(C=N1)C2=CC=C(NCCCNC-CNCCCNC)C=C2O
OC(C1=NN(C=N1)C2=CC=CC(OCCCCNCCCNCCCN(C)C)=CC=C2O)=O
O=C(OC)C1=NN(C=N1)C2=CC=C(OCCCCNC-CCNC)=C2O
OC(C1=NN(C=N1)C2=CC=C(OCCCCNCCCN(C)C)C=C2O)=O
OC(C1=NN(C=N1)C2=CC=C(OCCCCNCCCNC)=CC=C2O)=O
O=C(OC)C1=NN(C=N1)C2=CC=CC(NCCNCCN(C)C)=C2O
O=C(OCC)C1=NN(C=N1)C2=CC=C(OCCNCCNCCN(C)C)C=C2O
OC(C1=NN(C=N1)C2=CC=C(OCCCNCCCNCCCNC)=CC=C2O)=O
OC(C1=NN(C=N1)C2=CC=CC(NCCCNCCCNCCCN(C)C)=C2O)=O
O=C(OC(C)C)C1=NN(C=N1)C2=CC=C(NCCNC-NCCNCCNC)C=C2O
OC(C1=NN(C=N1)C2=CC=C(NCCCNCCCN(C)C)=CC=C2O)=O
OC(C1=NN(C=C1)C2=CC=CC(NCCNCCNCCN(C)C)=C2O)=O
O=C(OCC)C1=NN(C=C1)C2=CC=C(NCCNCCNCCN(C)C)C=C2O
OC(C1=NN(C=C1)C2=CC=C(NCCCNCCCN(C)C)=CC=C2O)=O
OC(C1=NN(C=C1)C2=CC=CC(NCCNCCNCCN(C)C)=C2O)=O
OC(C1=NN(C=C1)C2=CC=C(NCCNCCNCCN(C)C)C=C2O)=O
O=C(OC(C)C)C1=NN(C=C1)C2=CC=C(OCCCNCCCN(C)C)=CC=C2O
O=C(OC)C1=NN(C=C1)C2=CC=CC(OCCCCNC-CNCCCN(C)C)=C2O
OC(C1=NN(C=C1)C2=CC=C(OCCCCNCCCNCCCN(C)C)C=C2O)=O
O=C(OC(C)C)C1=NN(C=C1)C2=CC=CC(OCCCCNC-CCNC)=CC=C2O

OC(C1(C)CNC(C2=CC=CC(OCCCCNCCCNCCCN(C)C)=C2O)=N1)=O
O=C(OC(C)C)C1CNC(C2=CC=C(OCCNCCNCCNC-CNC)C=C2O)=N1
O=C(OC)C1(C)CNC(C2=CC(OCCCNCCCNCCCN(C)C)=CC=C2O)=N1
O=C(OCC)C1CNC(C2=CC=CC(NCCNCCNCCN(C)C)=C2O)=N1
OC(C1(C)CNC(C2=CC=C(NCCCNCCCNC)C=C2O)=N1)=O
OC(C1(C)CNC(C2=CC(NCCNCCNCCNCCN(C)C)=CC=C2O)=N1)=O
OC(C1COC(C2=CC=CC(OCCCCNCCCNCCCN(C)C)=C2O)=N1)=O
O=C(OCC)C1(C)COC(C2=CC=C(OCCCNCCCNC-CCNC)C=C2O)=N1
OC(C1(C)COC(C2=CC(OCCNCCNCCNCCN(C)C)=CC=C2O)=N1)=O
O=C(OC(C)C)C1(C)COC(C2=CC=CC(NCCNCCN(C)C)=C2O)=N1
OC(C1COC(C2=CC=C(NCCNCCN(C)C)C=C2O)=N1)=O
O=C(OC)C1(C)COC(C2=CC(NCCCNCCCNC)=CC=C2O)=N1

The activity of DADFT and DADFT-PE analogues as chelating agents may be illustrated in the following assays. Examples 1-8, as well as the compounds listed above which have not yet been made and/or tested, are predicted to have activity in these assays as well.

DISTRIBUTION AND SOLUBILITY STUDIES

A compound's physical properties may be used not only to characterize it but also to predict its suitability as a drug. Solubilities and distribution coefficients of Examples A, B, and 1-8 were determined and are reported below. It is predicted that certain compounds disclosed herein, including Examples 1-8, will be efficacious treatments for metal-mediated conditions.

Data Acquisition.

Measurements were taken via LC/MS. The LC system comprised a Waters ultra performance liquid chromatograph (UPLC) separation system equipped with sample organizer, column manager and heater/cooler, binary solvent manager, PDA detector and sample manager. Mass spectrometric analysis was performed using an API 4000 Qtrap instrument from AB Inc. with an ESI interface. The data acquisition and control system were created using Analyst 1.4.2 software from ABI.

LC/MS Conditions:

column: Phenomenex, Kinetex 2.6μ C18 (2.1×50 mm) coupled with preguard column; mobile phase: 0.1% formic acid in acetonitrile (A) and 0.1% formic acid in water (B); flow rate: 0.5 mL/min; column temperature: 35° C.; injection volume: 5 μL.

Mass Conditions:

Ion source: turbo spray; Ionization model: ESI; scan type: MRM; sollision gas: 6 L/min; curtain gas: 30 L/min (solubility) or 35 L/min (log D); nebulize gas: 50 L/min; auxiliary gas: 50 L/min; temperature: 500° C.; ionspray voltage: +5500 v (positive MRM) or −4500 v (negative MRM).

Log D Determination.

The distribution coefficient of compounds disclosed herein in was determined in octanol/PBS pH 7.4 by LC/MS/MS and reported as log D. Stock solutions of compounds were prepared in DMSO at the concentration of 30 mM. To each 5 μL aliquot of stock solution of each sample was added 500 μL of PBS pH 7.4 and 500 μL of octanol and a stir bar. Each vial was sealed and the Log D plate transferred to a plate shaker and shaken at 25° C. at 1,100 rpm for 1 hour. Stir bars were removed and samples centrifuged at 15,000 g for 15 minutes to separate the phases, and pipette and syringe were used to remove the upper (octanol) and lower (buffer) phases to empty tubes, respectively. Aliquots of 5 μL were taken from upper phases and diluted with 495 μL of methanol. Aliquots of 50 μL were taken from lower phases and diluted with 450 μL of methanol. Reference solutions of progesterone or metopolol were also prepared and tested as standards.

Solubility Determination.

Solubility of compounds disclosed herein in PBS pH 4.0 (near gastric pH) and PBS pH 7.4 (near plasma pH) were evaluated by LC/MS/MS. Stock solutions of test compounds were prepared in DMSO at the concentration of 30 mM. To each 10 μL aliquot of stock solution of each sample was added 990 μL of PBS pH 4.0 or PBS pH 7.4 and a stir bar. Vials were sealed and transferred to a plate shaker and shaken at 25° C. at 1100 rpm for 2 hours. Stir bars were removed and samples transferred to a filter plate and vacuum filtered. Aliquots of 10 μL were taken from filtrate and diluted with 990 μL of methanol. A reference standard of 3 μM diclofenac in DMSO was also prepared and tested.

Solubility was calculated as in Microsoft Excel as follows:

$$[Sample] = \frac{AREA_{sample} \times INJVOL_{Std} \times [STD]}{AREA_{Std} \times INJVOL_{sample} \times DF_{Std}}$$

Results are given below in Table 3. For the solubility determination, the assay upper limit was set at 300 μM; any value close to or above 300 μM indicates that the compound may have a solubility at or above 300 μM.

| Example | LogD | Solubility at pH 4.0 | at pH 7.4 |
|---|---|---|---|
| A | −1.14 | 308.97 | 304.77 |
| B | −1.45 | 307.4 | 313.07 |
| 1 | −1.39 | 308.76 | 312.34 |
| 2 | −1.77 | 296.62 | 291.45 |
| 3 | −1.87 | 301.98 | 299.36 |
| 4 | −2.13 | 312.85 | 316.23 |
| 5 | −2.09 | 306.48 | 311.25 |
| 6 | −1.98 | 310.52 | 310.54 |
| 7 | −2.24 | 293.70 | 296.83 |
| 8 | −2.14 | 299.54 | 297.58 |
| progesterone | 3.71 | — | — |
| metopolol | −0.27 | — | — |
| diclofenac | — | 7.47 | 273.38 |

IRON CLEARING EFFICIENCY AND CHELATION STUDIES

Cannulation of Bile Duct in Non-Iron-Overloaded Rats.

The cannulation has been described previously in Bergeron, R J et al., Blood 1993, 81, 2166-2173 and Bergeron, R J et al., Ann. N.Y. Acad. Sci. 1990, 612, 378-393. The bile duct is cannulated and fractions of bile are collected at intervals over a 24-48 hour period from male Sprague-Dawley rats (400-450 g) administered a single dose of drug by gavage. Urine is collected in a metabolic cage at similar time intervals. These biologic fluids are assayed for iron by atomic absorption or ICP. The kinetics of iron clearing and the total cumulative excreted iron is plotted for the purposes of comparing each compound. Sample collection and handling are as previously described.

Drug Preparation and Administration.

In the iron clearing experiments rats are given a single 50, 75, 150, or 300 µmol/kg dose of the test article drug po by gavage or sc. The compounds are administered as a solution in water or, depending on solubility, other suitable solvents such as DMSO at doses up to 300 µmol/kg dose only or (2) as the monosodium salt of the compound of interest (prepared by addition of the free acid to 1 equivalent of NaOH and titrated to neutrality with HCl as needed). The test article chelators are given to the primates or monkeys (*Cebus apella*, Cynomolgus, etc.) po by gavage or sc at a dose of up to 150 µmol/kg. The test article chelators are prepared as for the rats and given po by gavage or sc as a solution in water or other appropriate solvent system.

Calculation of Iron Chelator Efficiency.

ICE is calculated by dividing the total amount of iron excreted in bile and urine following a single dose of a given compound by the theoretical maximum amount of iron that could be bound based on the dose in moles. The theoretical iron outputs of the chelators are calculated with the understanding that the stoichiometry of this class of chelators is 2:1 ligand:iron complex. The iron clearing efficiencies of test article chelators in rats and monkeys are calculated as set forth in Bergeron, R J et al., *J. Med. Chem.* 1999, 42, 2432-2440. Data are presented as the mean +/− the standard error of the mean; p-values are generated via a one-tailed Student's t-test in which the inequality of variances is assumed; and a p-value of <0.05 is considered significant. Because there is a limited amount of chelatable iron available in an animal at any given time, the total iron clearance and iron-clearing efficiency of a chelator is saturable, i.e., as the dose of chelator increases, the iron clearing efficiency will reach a maximum and then decline as the total chelatable iron is bound to chelator and the remaining drug is excreted un-bound to iron. Thus, iron clearing efficiency is a function of absorption of the drug, the elimination of the drug and the plasma and cellular distribution of the drug to compartments that contain stored iron. For this reason, a number of standard doses are used in part to identify the point of point of saturation.

Chelator-Induced Iron Clearance and Iron Clearing Efficiency in Non-Iron-Overloaded Rodents:

Dose Response Studies. Iron clearing efficiency is first determined using the non-iron overloaded rat model. This model is suitable for determining the ferrokinetics, i.e., the time course of iron clearing over the dosing cycle as well as the duration of effect, i.e., the amount of time during which iron is eliminated in excess of background or baseline iron loss. The dose-response properties of the drug and the corresponding ferrokinetics of each compound when given po by gavage permit a direct comparison of compounds when determined in the non-iron-overloaded, bile duct-cannulated rodent model.

Iron-Clearing Efficiency in Non-Iron-Overloaded Rodents and Iron-Loaded Primates:

Oral versus Subcutaneous Administration. A similar protocol is executed in primates or monkeys to confirm consistent of results across species. A typical species for such studies would be *Cebus apella* monkeys in addition to the male Sprague-Dawley rats are used, 3-8 per group. Likewise, iron overloaded rats or monkeys can be used to determine ferrokinetics and dose response.

Similar to rats, monkeys held in a metabolic cage may be dosed by gavage at doses of between 25 µmol/kg and 300 µmol/kg. The iron clearing efficiency of each compound may be determined by averaging the iron output in stool and urine for 4 days before the administration of the test compound, subtracting these numbers from the two-day iron output in stool and urine following a single dose of the drug, and then dividing by the theoretical output; the result is expressed as a percent.

The above protocols and data are taken from Bergeron, R J et al., "Design, Synthesis, and Testing of Non-Nephrotoxic Desazadesferrithiocin Polyether Analogues," *J Med Chem.* 2008, 51(13), 3913-23 and US2010/0093812A1. Additional data pertaining to tissue distribution, toxicity, and pharmacokinetics can be found in these publications.

It is expected that certain compounds disclosed herein, including compounds chosen from Examples 1-8, will be effective in clearing iron in the assays above. An iron clearing efficiency (ICE) of greater than approximately 5% in rats or greater than approximately 5% in monkeys (such as *Cebus apella*) is considered sufficient to accomplish the daily therapeutic goals of iron chelation in an iron overloaded patient. Such an iron clearance exceeds deferoxamine (ICE=3%) which is the standard of care. An ICE in this range must be accompanied by an acceptable safety margin to allow dosing up to a suitable therapeutic effect. Higher ICE values for compounds can be beneficial. An ICE of greater than approximately 10% in rats or greater than approximately 10% in monkeys is considered very good, and an ICE of greater than approximately 20% in rats or greater than approximately 20% in monkeys is considered excellent assuming than in each case toxicity is not increasing with increasing ICE. An adequate ICE is the initial in vivo test that is used to identify iron chelators that might have clinical utility for the treatment of iron overload.

Comparable ICEs of a given compounds across multiple species is additionally predictive of clinical activity in human iron overloaded patients as compared to an adequate ICE in just one species. This relationship may be expressed as the ratio of the ICE in one species (e.g., monkey) to the ICE in another (e.g., rat). Deviations from a ratio of one in either direction suggest that the compound may have species-specific activity rather than generalizable activity in iron clearing. It is expected that certain compounds disclosed herein, including compounds chosen from Examples 1-8, will have favorable ICE ratios across species.

Examples A-F have been previously made and tested in the above assays, and their data, adapted from US2008/0214630A1, US2008/093812A1, WO2011/028255A2, and Bergeron, R. J. et al, *Biometals* 2011 April; 24(2):239-58, is reproduced below in Table 1.

TABLE 1

| Example | Rodent ICE [urine/bile] | Primate ICE [urine/bile] | ICE Ratio |
|---------|------------------------|--------------------------|-----------|
| A | 26.7 ± 4.7% [97/3] | 26.3 ± 9.9% [93/7] (capsule) | 1.0 |
|   |   | 28.7 ± 12.4% [83/17] (sodium salt) | 1.1 |
| B | 5.5 ± 1.9% [90/10] | 25.4 ± 7.4% [96/4] | 4.6 |
| C | 12.0 ± 1.5% [99/1] | 9.8 ± 1.9% [52/48] | 0.8 |
| D | 15.1 ± 2.0% [99/1] | 22.5 ± 6.4% [86/14] | 1.5 |
| E | 10.6 ± 4.4%b [95/5] | 23.0 ± 4.1% [95/5] | 2.2 |
| F | 12.4 ± 1.7% [98/2] | 9.6 ± 4.9% [25/75] | 0.8 |

Compounds that gain access to the intracellular erythrocyte compartment may been especially suited for the treatment of parasites such as malaria (*Plasmodium falciparum* and other spp.). Many parasites including those causing malaria cannot import iron in any form other than the free ferric or ferrous ionic form; iron chelators have been shown to have anti-malarial activity. Critical to this activity is the ability of the chelator to gain access to the interior of the red blood cell, the erythrocyte, either during its formation in the marrow or later. Assaying the ability of the chelator to enter red blood cells and chelate free iron would be a predictor of anti-malarial activity. It is expected that certain compounds disclosed herein, including compounds chosen from Examples 1-8, will exhibit the ability to enter red blood cells and chelate free iron to a degree sufficient to treat malaria.

LANTHANIDE AND ACTINIDE CHELATION STUDIES

The following protocols may be used to ascertain the activity of the compounds disclosed herein as chelators of lanthanides and actinides.

Cannulated Bile Duct Model.

It is also expected that certain compounds disclosed herein will be effective chelators of lanthanides and actinides. Uranium clearance studies may be carried out, for example, in a bile duct-cannulated rat model. See, e.g., US2010/0137346A1. In one protocol, the animals are given U(VI) (uranyl acetate dehydrate), Th(IV) (thorium tetrachloride), or Eu(III) (europium trichloride) SC such that the actual dose of uranium is 2.8 mg/kg, of thorium 2.7 mg/kg, and of europium 1.8 mg/kg. Test compounds may be given IP, SC or PO at times relative to lanthanide/actinide exposure (e.g., 0.5 hours prior to metal dosing, immediately upon such dosing, or 0.5, 1, 2, or 4 hours post-dosing). Bile and urine samples are collected at intervals over the 24 hours following dosing. Typical doses range from 100 to 600 µmol/kg initially with follow-on studies at 75 and 150 µmol/kg to identify the most potent chelators. Lanthanide/actinide content of the bile, urine, kidney, liver, lung and bone (femur) may all be collected. At least three animals are typically utilized in each experimental group. Data from separate control studies (e.g., uranyl acetate/no chelator) may also be collected. Metal concentrations may be measured using ICP/MS and data are typically reported as the total quantity of metal excreted [urine+bile]; the mode of excretion [urine/bile] may also be given. In addition, the percentage of the administered dose of metal cleared and chelator-induced metal excretion versus the controls may also be given. To be considered effective, the chelators must clear at least twice the amount of toxic metal compared to the metal excreted in untreated rats. The chelator DTPA serves as a positive control. The chelators that have the longest duration of action, i.e. continue to induce the excretion of toxic metal following a single dose, may be deemed the most promising chelators of lanthanides and actinides for clinical use.

Chelator analogues based on the desferrithiocin core have been tested in the above assay and have been found to be effective to different degrees depending on route of administration and timing of the dose, as disclosed in US '346 (see, e.g., Table 1 in that reference). For instance, Example B was evaluated in the assay above; five rats were tested against controls at 300 µmol/kg intraperitoneally dosed immediately after uranyl acetate. Results are given below in Table 2.

TABLE 2

| Example | Uranium Excretion µg/kg [urine/bile] | Uranium Excretion vs. Control | P vs. Control | % Dose Cleared |
|---------|--------------------------------------|-------------------------------|---------------|----------------|
| B | 626 ± 123 [35/65] | 2.2 | <0.001 | 22 |

Positive controls may also be evaluated for comparison. Four such controls were evaluated as disclosed in US '346: DTPA given as its trisodium calcium salt, DFO, N,N'-bis(2-hydroxybenzyl)ethylenediamine-N,N'-diacetic acid monosodium salt (NaHBED) and the hydroxypyridone CP94. Several of these controls were significantly active though the route of administration and the frequency of dosing differ.

It is expected that certain compounds disclosed herein, including compounds chosen from Examples 1-8, will be effective in clearing toxic metals from when tested in the assay above, and that they will be effective treatments for lanthanide or actinide overload.

Metabolic Model.

In another protocol, experiments are carried out in rats that have not had their bile duct cannulated. The animals are housed in metabolic cages. Urine and feces are collected at 24-h intervals. The lanthanide/actinide is given SC. Compounds are given to the rats by gavage, PO, or SC once daily for four days. The initial dose of the chelator is either given immediately after having been given the dose of metal or at some time after dosing, e.g., at 4 or 12 h after dosing. Additional doses of the chelator are given once daily for three more days. One day post last dose the animals are sacrificed and the metal content of the urine, feces, kidney, liver, lung and bone are determined. In each case, progression to a longer time interval, e.g., 4 or 12 h, depends on the decorporation of a minimum of twice the metal excreted by the metal only treated rats. The chelator DTPA serves as a positive control. Target organs of metal toxicity—kidney and liver—are histopathologically examined to determine if lanthanide/actinide-induced renal or hepatotoxicity has been mitigated.

MRI Studies.

MRI studies of europium distribution after intratracheal or intravenous administration of metals including europium may also be conducted as described in US '346 at paragraph [0064].

Primate Studies.

Lanthanide/actinide clearance studies may also be conducted in primates following the procedure described in US '346 (citing Bergeron, et al., *Comp Med.* 2004; 54:664-672) with some modifications. In that protocol, five primates are given Eu(III) SC at a dose of 0.5 mg/kg. Three animals are given a chelator and two additional monkeys serve as Eu(III) controls. Initially, the decorporation agent may be administered PO at a dose of 300 µmol/kg 1 h post Eu(III). Urine and stool are collected for three days and assessed for their metal content. The animals are rested for 14 d and the experiment repeated with the chelator given 2 h post metal exposure, and the cycle is repeated next at 4 h post Eu(III) exposure. Fourteen days later, in a final experiment, the same 5 animals are given U(VI) and Th(IV) SC, each at a dose of 0.5 mg/kg. One hour post metal exposure, three of the monkeys are given a chelator PO at a dose of 300 µmol/kg. Two animals will serve as U(VI) and Th(IV) controls. The choice of chelator may be based on rodent studies; the ligand which decorporates both Th(IV) and U(VI) most effectively being selected. Urine and feces are collected for two days post drug (longer collection times are less feasible, as primate metabolic cages typically must be cleaned every day). After this experiment, all five primates are euthanized and levels of U(VI), Th(IV) and Eu(III), as well as chelator, measured in kidney, liver, lung, and bone using ICPMS. Again, to be considered effective, animals receiving compound will typically excrete twice or more the lanthanide/actinide as compared to control animals. It is expected that certain compounds disclosed herein, including compounds chosen from Examples 1-8, will exhibit favorable lanthanide/actinide chelation.

The protocol employed in Rao L, Choppin G R, and Bergeron R J, *Radiochim. Acta.* 88, 851-856 (2000) may also be used, optionally with adaptations clear to those of skill in the art, to ascertain the activity of compounds as chelators of lanthanides and actinides. Compounds disclosed herein are expected to show efficacy in this assay.

Because inhalation is one of the anticipated principal routes of potential lanthanide or actinide contamination (for example via a "dirty bomb" or other radioactive weapon, or via nuclear contamination following a reactor meltdown), it may be particularly useful to assay compound and metal accumulation in the lung tissue. A more lipophilic compound would be expected to accumulate in the lung tissue to a greater degree than a more hydrophilic one. See, e.g., Bergeron, et al., *Medicinal Inorganic Chemistry* 2005; 366383.

TOXICOLOGY AND PHARMACOKINETIC STUDIES

The use of metal chelating agents has historically been limited by toxicity; typical targets of toxicity have been bone marrow, liver, kidney and neurologic tissues. Increasing lipophilicity of chelators is positively correlated with increased iron-clearing efficiency, that is, the greater the log $p_{app}$ value of the compound, the greater the iron clearing efficiency (ICE) presumably because the intracellular concentration of chelator is higher and gaining access to the major source of stored iron; however, lipophilicity of chelators is also correlated with toxicity because iron is an essential element and prolonged intracellular depletion of iron will impair cell physiology and ultimately lead to apoptosis and cell death. Other properties such as bioavailability are adversely affected with increasing lipophilicity. Therefore, these competing properties of a chelator must be assessed individually; a clinical candidate is one in which the absorption, metabolism, distribution and excretion permit adequate iron chelation without compromising normal iron metabolism. In any event, compounds disclosed herein may additionally be tested in standard animal toxicology studies to determine maximum tolerable doses, efficacious doses, and to predict suitable doses in humans. Short-term and long toxicology term studies are well-known by those of skill in the art.

Additionally, compounds disclosed herein may be tested in standard pharmacokinetic assays in order to determine which compounds have appropriate characteristics, such as half life, oral bioavailability, tissue distribution, and the like, for particular applications. Such studies are typically conducted in vivo in rodents and other species, but may also be in vitro, using, for example, liver microsomes to determine metabolic stability and to identify any potentially active metabolites.

In Vivo Nephrotoxicity Study.

A preliminary dose-range finding study may be used in which male Sprague-Dawley rats are given test article once daily by gavage for 7-14 days at doses of 75, 150, 300 or 450 µmol/kg/dose/day. Histopathological analysis is then performed to assess vacuolization in the renal proximal tubules at all doses.

Once the dose is selected, a total of 12 rats may be used to test two compounds, for example: four controls, four treated with one compound, and four treated with another. The compounds are given po by gavage to the rodents once daily for 7-14 days at equimolar doses. At the end of the dosing period, the kidneys are perfusion-fixed and one kidney from each rat is dissected. Tissue samples of 1 mm$^3$ are cut from the kidney cortexes and the proximal and distal tubules are examined under light microscopy. The kidneys from the control animals should show normal proximal tubular architecture. The proximal tubules of kidneys from the rodents treated with a relatively non-toxic test article will be indistinguishable from those of the control animals. Animals treated with a more renotoxic test article may show regional, moderate-to-severe vacuolization in the proximal tubules often the S3 segment, a loss of the brush border, and/or tubular extrusions toward the lumen; the distal tubules may show moderate-to-severe vacuolization. Under electron microscopy the kidneys from the control animals will show normal proximal and distal tubular architecture. Kidneys from animals treated with a relatively non-toxic test article may present with occasional vacuolization and apoptotic nuclei and have some abnormal giant lysosomes at the basolateral side of the proximal tubule but are otherwise normal. The same is true of the distal tubules. Finally, animals treated with a more renotoxic test article may show regional, moderate-to-severe vacuolization of the proximal tubules loss of the brush border, Golgi dilations, tubular extrusions toward the lumen, and apoptotic nuclei. The distal tubules may demonstrate moderate-to-severe vacuolization. While the distal tubules of both the toxic and non-toxic treated animals may demonstrate some vacuolization, the changes to the kidneys of the animals treated with a toxic test article are much more pronounced.

In Vitro Pharmacokinetic Stability Evaluation.

Test article compounds may be tested for metabolic stability in human whole blood. Such testing is commonly undertaken prior to or along with advanced preclinical testing in order to identify compounds with desirable pharmacokinetic properties. In an exemplary protocol, into each of 6 centrifuge tubes is added 2 µL of test compound and 198 µL of human whole blood, taken from normal, healthy volunteers, to achieve a final concentration of 5 µM. Tubes are then incubated at 37° C. at approximately 100 rpm on an orbital shaker. One of the tubes is taken at designated time points including 0, 0.5, 1, 4, 6 and 24 hours. The reaction is stopped by the addition of 4 volumes of cold methanol. Samples are centrifuged at 20,000 rpm for 20 minutes to precipitate protein. A 200 µL aliquot of the supernatant is used for LC/MS/MS analysis for each compound at each time point. Experiments may be performed in duplicate to ensure reliability. The LC system may comprise, for example, a Shimadzu liquid chromatograph separation system equipped with degasser DGU-20A3, solvent delivery unit LC-20AD, system controller CBM-20A, column oven CTO-10ASVP and CTC Analytics HTC PAL System. Mass spectrometric analysis may be performed using an API 4000 instrument from AB Inc. (Canada) with an ESI interface. A data acquisition and control system may be employed using Analyst 1.5 software from ABI Inc. Calculations may be carried out using Microsoft Excel. Percent compound remaining at each time point may be estimated by determining the peak areas from extracted ion chromatograms. The half-life of compound in human whole blood can be measured in this way. It is expected that certain compounds disclosed herein, including compounds chosen from Examples 1-8, will have a sufficiently long half-life to be useful as treatments ailments including for metal overload and related disorders.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having a structural formula chosen from the group consisting of IIIa, IIIb, IIIc and IIId:

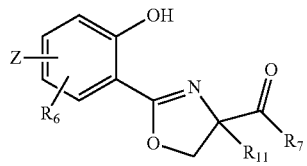
IIIa

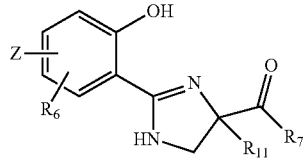
IIIb

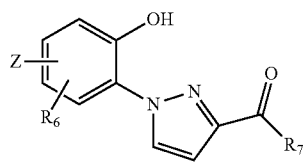
IIIc

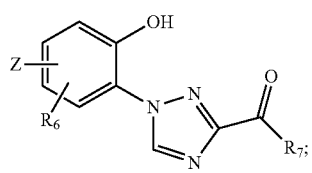
IIId or a salt thereof, wherein:
Z is chosen from $OR_1$, $NR_2R_3$, morpholine, and optionally substituted piperazine;
$R_1$ is chosen from $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_2$ is chosen from hydrogen, alkyl, $[(CH_2)_m-O]_x-[(CH_2)_n-O]_y-R_4$, $[(CH_2)_m-NH]_x-[(CH_2)_n-NR_4]_y-R_5$, and $[(CH_2)_m-O]_x-[(CH_2)_n-NR_4]_y-R_5$;
$R_3$ is chosen from hydrogen and alkyl;
each m and each n is, independently, an integer from 1 to 8;
x is an integer from 0 to 8;
y is an integer from 1 to 8;
$R_4$ and $R_5$ are independently chosen from hydrogen, alkyl, and acyl;
$R_6$ is chosen from hydrogen, alkyl and alkoxy;
$R_7$ is chosen from $OR_8$ and $N(OH)R_9$;
$R_8$ is chosen from hydrogen, alkyl and aralkyl;
$R_9$ is chosen from an alkyl group and $-(CH_2)_p-N(OH)C(O)R_{10}$;
p is an integer from 1 to 8;
$R_{10}$ is an alkyl group; and
$R_{11}$ is chosen from hydrogen and alkyl.

2. The compound as recited in claim 1, having a structural formula chosen from the group consisting of IIIa1, IIIa2, IIIa3, IIIb1, IIIb2, IIIb3, IIIc1, IIIc2, IIIc3, IIId1, IIId2, and IIId3:

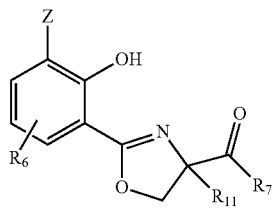
IIIa1

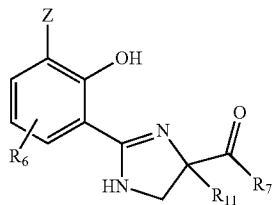
IIIa2

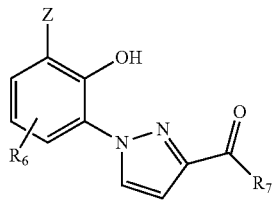
IIIa3

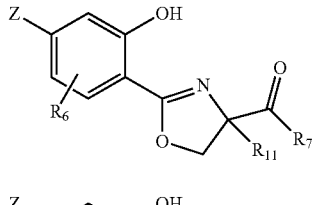
IIIb1

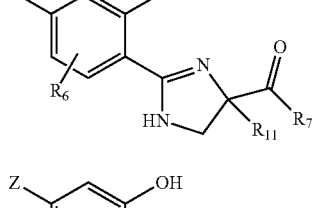
IIIb2

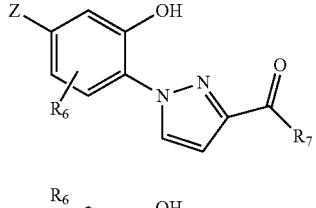
IIIb3

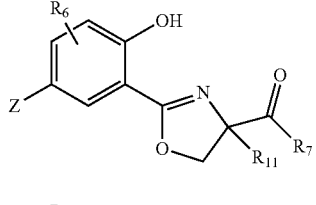
IIIc1

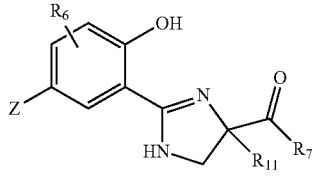
IIIc2

-continued

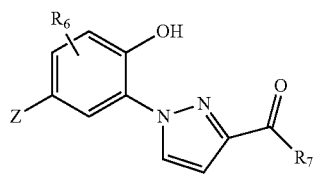

IIIc3

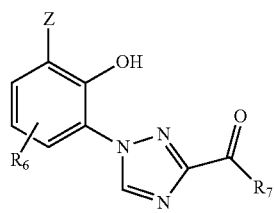

IIId1

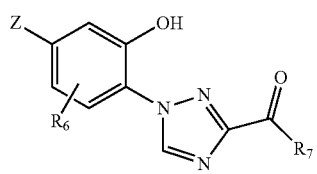

IIId2

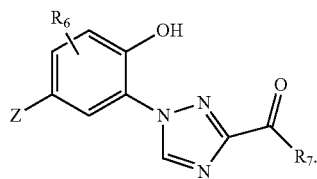

IIId3

3. The compound as recited in claim 2, wherein Z is $OR_1$.

4. The compound as recited in claim 3, wherein $R_1$ is $[(CH_2)_m-O]_x-[(CH_2)_x-O]_y-R_4$.

5. The compound as recited in claim 4, wherein:
each m and each n is, independently, an integer from 1 to 4;
x is an integer from 0 to 4; and
y is an integer from 1 to 4.

6. The compound as recited in claim 5, wherein $R_4$ is alkyl.

7. The compound as recited in claim 6, wherein:
each n is, independently, an integer from 2 to 3;
x is 0; and
y is an integer from 1 to 4.

8. The compound as recited in claim 7, wherein $R_4$ is lower alkyl.

9. The compound as recited in claim 8, wherein $R_7$ is $OR_8$.

10. The compound as recited in claim 9, wherein:
each n is 2;
x is 0;
y is an integer from 2 to 3; and
$R_4$ is methyl.

11. The compound as recited in claim 10, wherein $R_8$ is hydrogen.

12. A compound selected from the group consisting of:

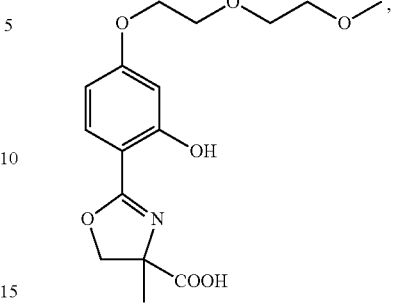

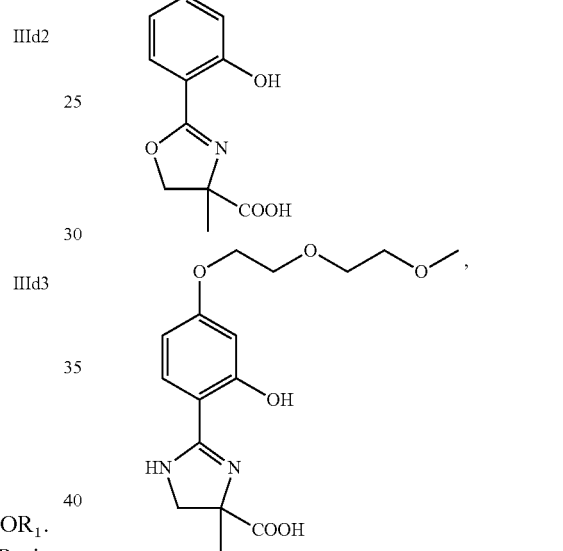

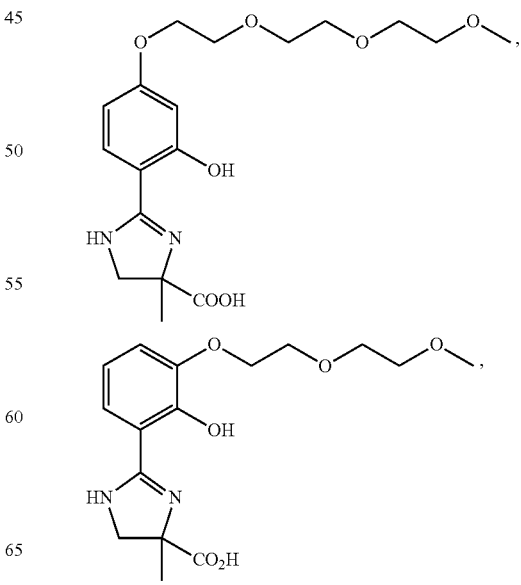

83
-continued
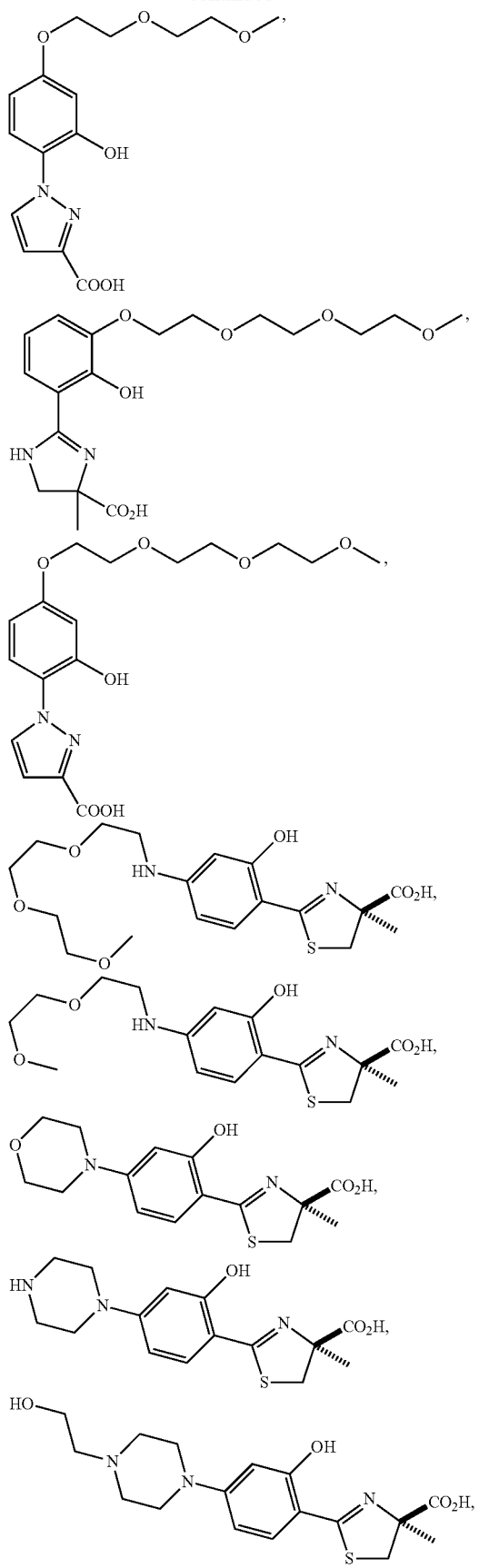
84
-continued
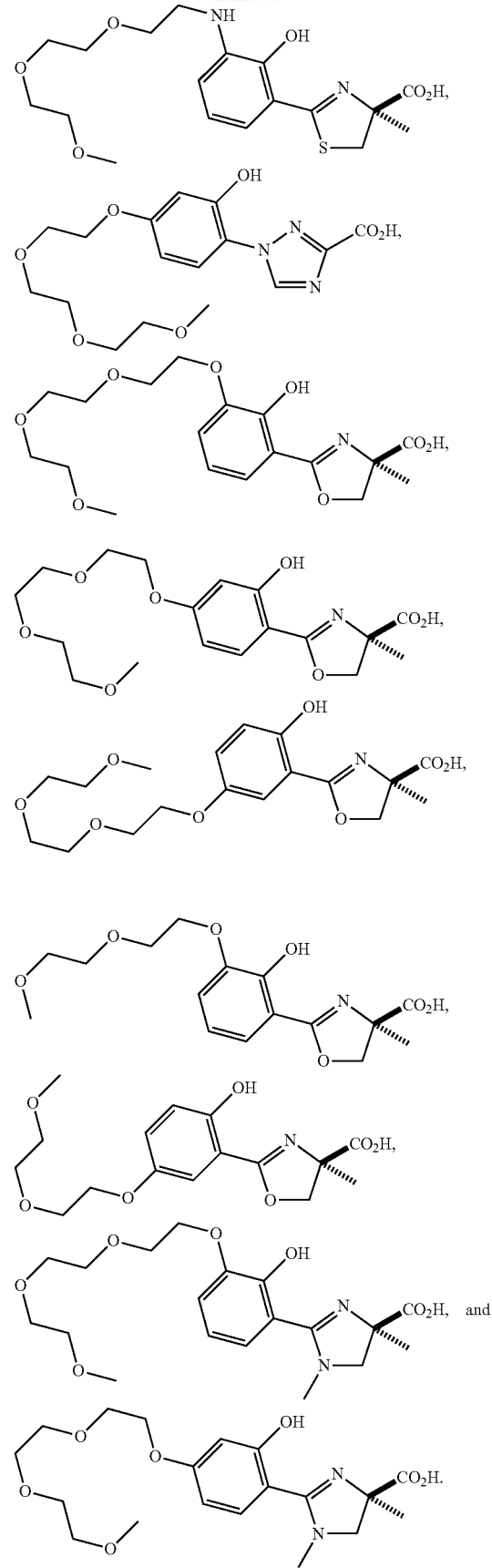

13. The compound as recited in claim 12, chosen from:
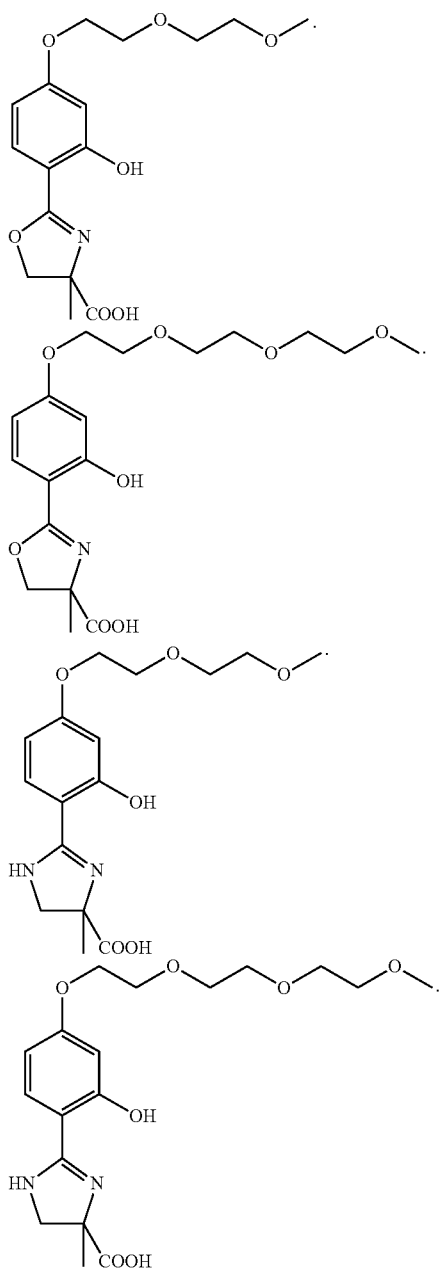
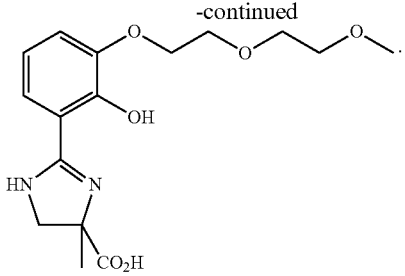
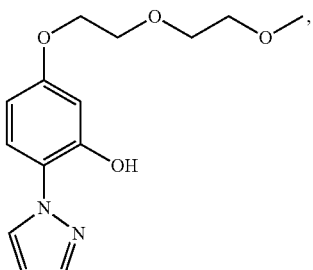
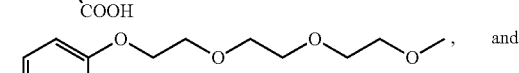
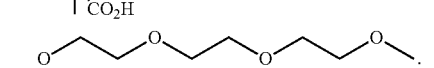
14. A pharmaceutical composition comprising the compound as recited in claim 1, together with at least one pharmaceutically acceptable excipient.
* * * * *